US010068331B2

(12) United States Patent
Hansen et al.

(10) Patent No.: US 10,068,331 B2
(45) Date of Patent: Sep. 4, 2018

(54) SYSTEM AND APPARATUS FOR REAL-TIME PROCESSING OF MEDICAL IMAGING RAW DATA USING CLOUD COMPUTING

(71) Applicant: The United States of America, as Represented by the Secretary, Dept. of Health and Human Services, Washington, DC (US)

(72) Inventors: Michael S. Hansen, Bethesda, MD (US); Hui Xue, Bethesda, MD (US); Peter Kellman, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 93 days.

(21) Appl. No.: 15/115,839

(22) PCT Filed: Feb. 3, 2015

(86) PCT No.: PCT/US2015/014252
§ 371 (c)(1),
(2) Date: Aug. 1, 2016

(87) PCT Pub. No.: WO2015/117129
PCT Pub. Date: Aug. 6, 2015

(65) Prior Publication Data
US 2017/0169564 A1 Jun. 15, 2017

(51) Int. Cl.
G06K 9/00 (2006.01)
G06T 7/00 (2017.01)
G01R 33/56 (2006.01)
G01R 33/561 (2006.01)
G01R 33/563 (2006.01)
G01R 33/567 (2006.01)
G01T 1/164 (2006.01)
H04L 29/08 (2006.01)

(52) U.S. Cl.
CPC ........ G06T 7/0012 (2013.01); G01R 33/5608 (2013.01); G01R 33/5611 (2013.01); G01R 33/5673 (2013.01); G01R 33/56341 (2013.01); G01T 1/1642 (2013.01); H04L 67/10 (2013.01); G06T 2207/10081 (2013.01); G06T 2207/10088 (2013.01)

(58) Field of Classification Search
CPC ............ G01R 33/5608; G01R 33/5611; G01R 33/56341; G01R 33/5673; G01T 1/1642; G06F 19/321; G06T 7/0012; G06T 2207/10081; G06T 2207/10088; H04L 67/10
USPC .......................................................... 382/131
See application file for complete search history.

(56) References Cited

U.S. PATENT DOCUMENTS

| | | | |
|---|---|---|---|
| 9,121,926 B2* | 9/2015 | Nair | A61B 8/06 |
| 9,747,421 B2* | 8/2017 | Krishna | A61B 5/7257 |
| 2013/0060579 A1* | 3/2013 | Yu | G06Q 10/06 |
| | | | 705/3 |
| 2014/0350962 A1* | 11/2014 | Robinson | G06F 19/3487 |
| | | | 705/3 |

(Continued)

Primary Examiner — Mekonen Bekele
(74) Attorney, Agent, or Firm — Polsinelli PC; Ron Galant

(57) ABSTRACT

The present invention relates to a system and apparatus for managing and processing raw medical imaging data.

20 Claims, 25 Drawing Sheets

(56) References Cited

U.S. PATENT DOCUMENTS

| | | | |
|---|---|---|---|
| 2015/0237106 A1* | 8/2015 | Golay | H04L 67/02 709/203 |
| 2016/0004820 A1* | 1/2016 | Moore | H04W 4/21 705/3 |
| 2016/0224805 A1* | 8/2016 | Patti | G06F 21/6254 |
| 2016/0299936 A1* | 10/2016 | Chavda | G06F 11/36 |
| 2016/0358333 A1* | 12/2016 | Lee | G06T 7/0012 |
| 2017/0076043 A1* | 3/2017 | Dormer | G06F 19/321 |
| 2017/0124730 A1* | 5/2017 | Forman | G06T 11/003 |
| 2017/0168812 A1* | 6/2017 | Golay | G06F 8/654 |

* cited by examiner (a) GRAPPA  (b) l1-SPIRiT (a) GRAPPA  (b) l1-SPIRiT

FIG 13
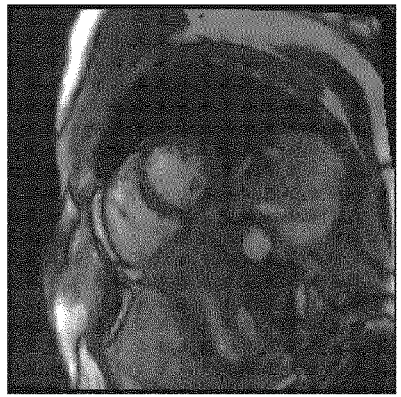

FIG. 18
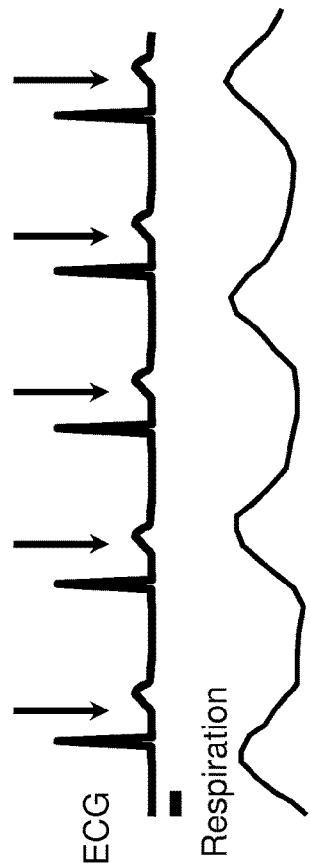
ECG
Respiration
TSENSE (R=4)
Improved temporal resolution
But only works for Cartesian sampling
Re-binning of data
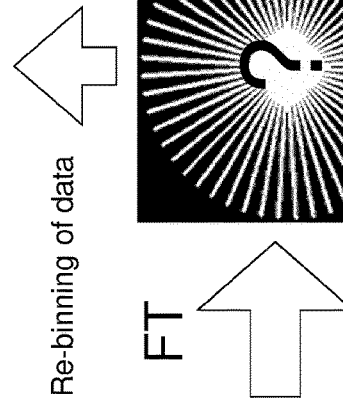
FT
Non-Rigid Registration
Single Cardiac Phase 192x128 matrix, 30 ms/frame, acquisition time 16s per slice 192x128 matrix, 30 ms/frame, acquisition time 16s per frame Assembly Principle

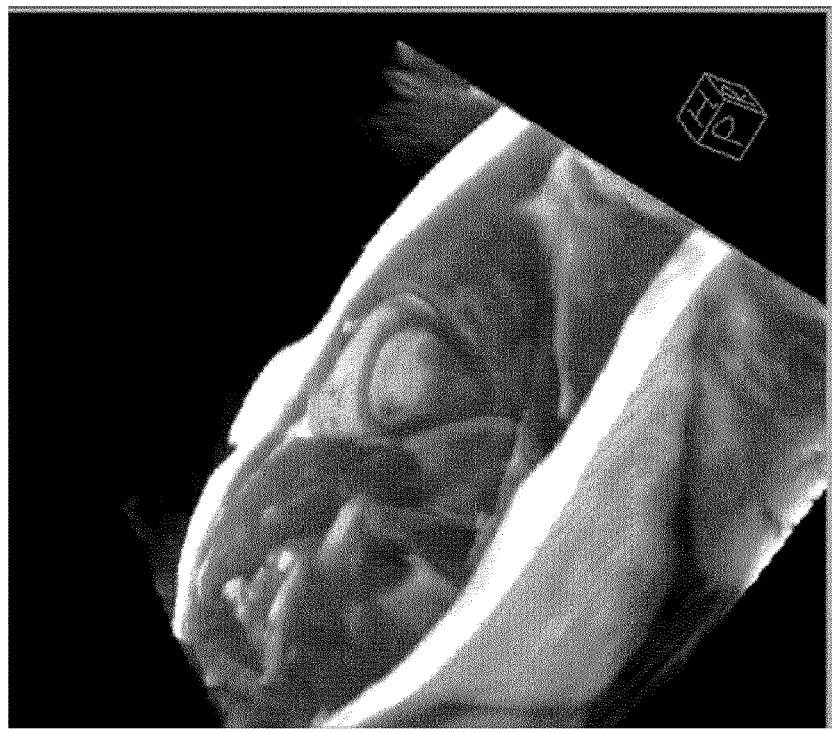
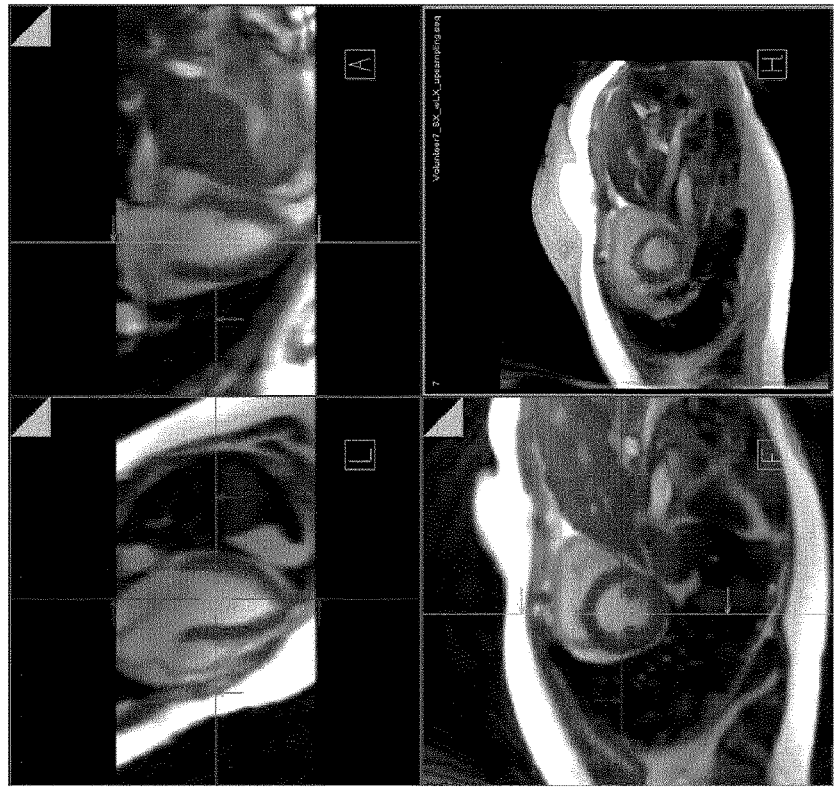
FIG. 25
4D Assembly (SX)

SYSTEM AND APPARATUS FOR REAL-TIME PROCESSING OF MEDICAL IMAGING RAW DATA USING CLOUD COMPUTING

The computing process (image formation from raw data) in medical imaging has become increasingly complex with high computational demands. The computational equipment (in general a single computer) deployed with clinical imaging systems is often inadequate for achieving clinically practical image reconstruction times. The hardware has to be specified and tested years before the imaging devices are deployed and the hardware is consequently obsolete before it is deployed. After the imaging data is acquired, one or more processing steps are performed to reconstruct an image using the imaging data. Conventional processing systems are located proximate to the image acquisition hardware (e.g., ultrasonic scanner, magnetic resonance imaging (MRI), and computed tomography (CT)). This processing raw image data may be quite intensive in nature, and may require significant processing capability.

Aspects of the present system and apparatus eliminate the need to deploy data processing hardware locally by deploying the image reconstruction hardware and software in a (remote) cloud computing system. The powerful computational resources available in commercial cloud systems can be leveraged directly in modem medical imaging devices and by doing so, the image processing hardware is replaced by a flexible software component, which can be scaled on-the-fly to match modem algorithms and which can be serviced and deployed remotely. For the end-user of imaging device, e.g. the physician or technician operating the scanner, they will feel no differences than if the computation was performed locally. We have demonstrated that this is possible with clinical MRI systems and using this paradigm, image reconstruction can be sped up by an order of magnitude for some applications.

Additional detail and description of the functionality of the system and apparatus for managing and/or processing of medical imaging raw, according to aspects of the present invention, is provided herein.

BRIEF DESCRIPTION OF THE DRAWINGS

FIGS. 11-25 show that (1) breath holds should not be necessary; (2) function can be evaluated with parallel imaging alone; (3) more advanced techniques may be needed for higher resolution with high frame rate; and (4) real-time series can be motion corrected and combined for improved temporal resolution.

FIG. 11 depicts how free breathing leads to true real-time function and motion compensation.

FIG. 12 depicts parallel imaging for reduced breath-hold and real-time free-breathing acquisition with improved temporal resolution.

FIG. 13 depicts real-time function examples.

FIG. 14 depicts k-t Sparse reconstruction for cardiac real-time CINE MRI. Iterative k-t sparse reconstruction might become a key enabler for cardiac real-time CINE MRI. The proposed protocol is CINE TrueFISP, 1.5T, ECG triggered, net acceleration 9.2, 16 heart-beats for 8 slices, spatial resolution 2.2 (2.6)×2.2×8 $mm^3$, and temp. resolution 30 ms. The aim is reconstruction time ~15 s per slice. The volunteer is 135 kg, 176 cm, BMI 43.

FIG. 15 depicts gadgetron scanner integration. Hansen and Sorensen, Magnetic Resonance in Medicine 69(6), 1768-1776.

FIG. 16 depicts deployment of gadgetron in the cloud.

FIG. 17 depicts cloud based Gadgetron reconstruction.

FIG. 18 depicts improving real-time cardiac MRI. Kellman et al., Magn. Res. Med. 2009; Hansen et al., Magn. Reson. Med. 2012.

FIG. 19 depicts the motivation for non-Cartesian acquisition. The Golden Angle Trajectory is used. Each subsequent profile is rotated 111.23 degrees from previous, and temporal resolution can be adjusted dynamically.

FIG. 20 depicts how the reconstruction problem is solved by including motion into an iterative reconstruction algorithm. Hansen et al., Magn. Reson. Med. 2012.

FIG. 21 depicts the how reconstruction can be applied to Cartesian and non-Cartesian trajectories.

FIG. 22 depicts non-linear binning reconstruction. Xue et al., JCMR 15:102, 2013.

FIG. 23 depicts non-linear binning reconstruction. Xue et al., JCMR 15:102, 2013.

FIG. 24 depicts an assembly principle, with volume reconstruction at one cardiac phase with four major steps: (1) anchor selection, (2) slice selection with anchors, (3) non-rigid slice correction, and (4) scattered interpolation.

FIG. 25 depicts 4D assembly (SX), reconstruction for SX stack with LX slices as the anchors.

EXAMPLE 1

Figure 1:
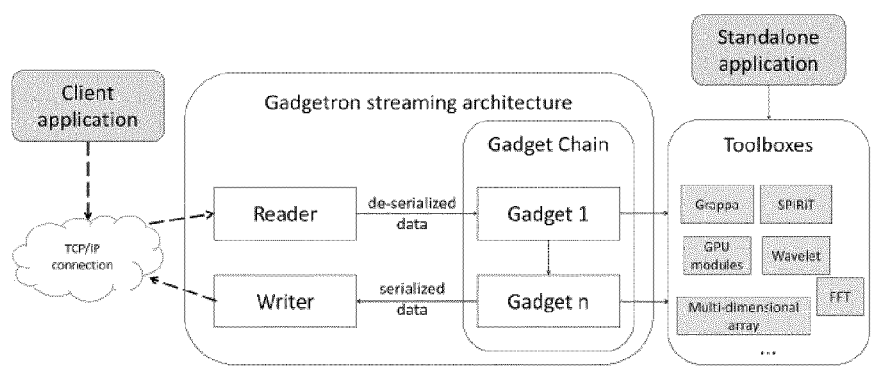
FIG. 1A depicts a schematic presentation of Gadgetron architecture. The client application communicates with Gadgetron process via the TCP/IP connection. The Reader de-serializes the incoming data and passes them through the Gadget chain. The results are serialized by the Writer and sent back to client application. The Gadgetron process resides on one computer, the Gadgetron server. The client can be a MRI scanner or other customer processes. Note the algorithm modules implemented in the Gadgetron toolboxes are independent from the streaming framework. Therefore, these functionalities can be called by standalone applications which are not using the streaming framework.

Distributed MRI Reconstruction Using Gadgetron Based Cloud Computing

Purpose:
To expand the Open Source Gadgetron reconstruction framework to support distributed computing and to demonstrate that a multi-node version of the Gadgetron can be used to provide non-linear reconstruction with clinically acceptable latency.

Methods:
The Gadgetron framework was extended with new software components that enable an arbitrary number of Gadgetron instances to collaborate on a reconstruction task. This cloud-enabled version of the Gadgetron was deployed on three different distributed computing platforms ranging from a heterogeneous collection of commodity computers to the commercial Amazon Elastic Compute Cloud. The Gadgetron cloud was used to provide non-linear, compressed sensing, reconstruction on a clinical scanner with low reconstruction latency for example cardiac and neuro imaging applications.

Results:
The proposed setup was able to handle acquisition and l1-SPIRiT reconstruction of nine high temporal resolution real-time, cardiac short axis cine acquisitions, covering the ventricles for functional evaluation, in under one minute. A three-dimensional high-resolution brain acquisition with 1 $mm^3$ isotropic pixel size was acquired and reconstructed with non-linear reconstruction in less than five minutes.

Conclusion:
A distributed computing enabled Gadgetron provides a scalable way to improve reconstruction performance using commodity cluster computing. Non-linear, compressed sensing reconstruction can be deployed clinically with low image reconstruction latency.

Introduction
Image reconstruction algorithms are an essential part of modern medical imaging devices. The complexity of the reconstruction software is increasing due to the competing demands of improved image quality and shortened acquisition time. In the field of MR imaging, in particular, the image reconstruction has advanced well beyond simple fast Fourier transforms to include parallel imaging (1-5), non-linear reconstruction (6,7) and real-time reconstruction (8,9). The increased interest in 3D acquisitions and non-Cartesian sampling has increased the computational demands further. For applications where lengthy acquisition and reconstruction time is prohibited by physiological motion, biological processes, or limited patient cooperation, the reconstruction system is under further pressure to deliver images with low latency in order to keep up with the ongoing study.

While the need for fast image reconstruction is growing, most published reconstruction algorithms, especially those relying on iterative solvers, such as image domain compressive sensing (6,10-12) and k-space SPIRiT and its regularized versions (7,13,14), do not come with the efficient reference implementations that would enable clinical use. In many cases, the algorithms are not implemented for online use on clinical scanners. Even if the developers would like to integrate their reconstruction algorithms for online use, the vendor provided hardware and software platform may have inadequate specifications for a demanding reconstruction or the available programming window may be unsuited for integration of new reconstruction schemes. Consequently, there is a gap between the number of new algorithms being developed and published and the clinical testing and validation of these algorithms.

Undoubtedly, this is having an impact on the clinical adoption of novel non-linear reconstruction approaches (e.g. compressed sensing).

We have previously introduced an open-source platform for medical imaging reconstruction algorithms called the Gadgetron (15), which aims to partial address the above-mentioned concerns. This platform is freely available to the research community and industry partners. It is platform independent and flexible for both prototyping and commercial development. Moreover, interfaces to several commercial MR platforms have been developed and are being shared in the research community. This simplifies the online integration of new reconstruction algorithms significantly and the new algorithms in research papers can be tested in clinical settings with less implementation effort. As a result, some groups have used Gadgetron for online implementation and evaluation of their reconstruction methods (16-18). Since the publication of the first version of the Gadgetron, the framework has adopted a vendor independent raw data format, the ISMRM Raw Data (ISMRMRD) format (19). This further enables sharing of reconstruction algorithms.

While this concept of an open-source platform and a unified ISMRMRD format shows great potential, the original Gadgetron framework did not support distributed computing across multiple computational nodes. Although the Gadgetron was designed for high performance (using multiple cores or GPU processors), it was originally implemented to operate within a single node or process. Distributed computing was not integral to the design. As reconstruction algorithms increase in complexity they may need computational power that would not be economical to assemble in a single node. The same considerations have led to the development of commodity computing clusters where a group of relatively modest computers are assembled to form a powerful computing cluster. An example of such a cluster system is the National Institutes of Health Biowulf Cluster (http://biowulf.nih.gov). Recently commercial cloud based services also offer the ability to configure such commodity computing clusters on demand and rent them by the hour. The Amazon Elastic Compute Cloud (EC2) is an example of such a service (http://aws.amazon.com/ec2).

In this paper, we propose to extend Gadgetron framework to enable cloud computing on multiple nodes. With this extension (named "Gadgetron Plus or GT-Plus"), any number of Gadgetron processes can be started at multiple computers (referred to as 'nodes') and a dedicated inter-process controlling scheme has been implemented to coordinate the Gadgetron processes to run on multiple nodes. A large MRI reconstruction task can be split and run in parallel across these nodes. This extension to distributed computing maintains the original advantages of Gadgetron framework. It is freely available and remains platform independent. As demonstrated in this paper, the nodes can even run different operating-systems (e.g. Windows or different distribution of Linux) and have different hardware configurations.

The implemented architecture allows the user to set up a GT-Plus cloud in a number of different ways. Specifically, it does not require a dedicated professional cloud computing platform. The GT-Plus cloud can be deployed on setups ranging from an arbitrary collection of networked computers in a laboratory (we refer to this as a "casual cloud") to high end commercial cloud systems, as demonstrated in the following. In this paper, we demonstrate the GT-Plus cloud set up in three different scenarios and demonstrate its flexibility to cope with variable computational environments. The first cloud setup is a "casual cloud", consisting of seven personal computers situated in our laboratory at the National Institutes of Health. The second setup uses NIH's Biowulf Cluster (20). The last configuration is deployed on the commercial Amazon Elastic Compute Cloud (Amazon EC2) (21).

To demonstrate the benefits of this extension, we used the cloud enabled version of the Gadgetron to implement non-linear l1-SPIRiT (7) for 2D time resolved (2D+t) and 3D imaging applications. We demonstrate that cardiac cine imaging with 9-slices covering the entire left ventricle (32 channels, acquired temporal resolution 50 ms, matrix size 192×100, acceleration factor 5, ~1.5 s per slice) can be reconstructed with l1-SPIRiT with a reconstruction time (latency <30 s) that is compatible with clinical workflow. Similarly we demonstrate high resolution 3D isotropic brain scans (20 channels, matrix size 256×256×192, acceleration factor 3×2, 1 mm$^3$ isotropic acquired resolution), can be reconstructed with non-linear reconstruction with clinically acceptable latency (<2.5 mins). For both cases, significant improvement of image quality is achieved with non-linear reconstruction compared to the linear GRAPPA results.

In the following sections, details of GT-Plus design and implementation are provided. The referral to specific source code components such as C++ classes, variables, and functions is indicated with monospaced font, e.g. GadgetCloudController.

Methods

Architecture and Implementation

In the following sections, we will first briefly review the Gadgetron architecture and the extensions that have been made to this architecture to enable cloud computing. Subsequently, we will describe two specific types of MRI reconstructions (2D time resolved imaging and 3D imaging) that have been deployed on this architecture.

Gadgetron Framework

The Gadgetron framework is described in detail in (15). Here we briefly review the dataflow for comparison to the cloud based dataflow introduced below. As shown in FIG. 1, A Gadgetron reconstruction process consists of three components: Readers, Writers and Gadgets. A Reader receives and de-serializes the incoming data sent from the client (e.g. a client can be the MR scanner). A Writer serializes the reconstruction results and sends the data packages to the client. The Gadgets are connected to each other in a streaming framework as processing chains.

The Gadgetron maintains the communication with clients using a TCP/IP socket based connection. The typical communication protocol of Gadgetron process is the following:
 a) The client issues the connection request to the Gadgetron server at a specific network port.
 b) The Gadgetron accepts the connection and establish the TCP/IP communication.
 c) The client sends an XML based configuration file to the Gadgetron server. This XML configuration outlines the Reader, Writers, and Gadgets to assemble a Gadget chain.
 d) The Gadgetron server loads the required Readers, Writers and Gadgets from shared libraries as specified in the configuration file.
 e) The client sends an XML based parameter file to the Gadgetron. The Gadgetron can initialize its reconstruction computation based on the parameters (e.g. acquisition matrix size, field-of-view, acceleration factor etc.). For MRI this XML parameter file is generally the ISMRMRD XML header describing the experiment.
 f) The client sends every readout data to the Gadgetron in the ISMRMRD format. These data are de-serialized by the Reader and passed through the Gadget chain.
 g) The reconstruction results are serialized by the Writer and send back to the client via the socket connection.
 h) When the end of acquisition is reached, the Gadgetron closes down the Gadget chain and closes the connection when the last reconstruction result has been passed back to the client.

Gadgetron Plus (GT-Plus): Distributed Computing Extension of Gadgetron

Figure 2:
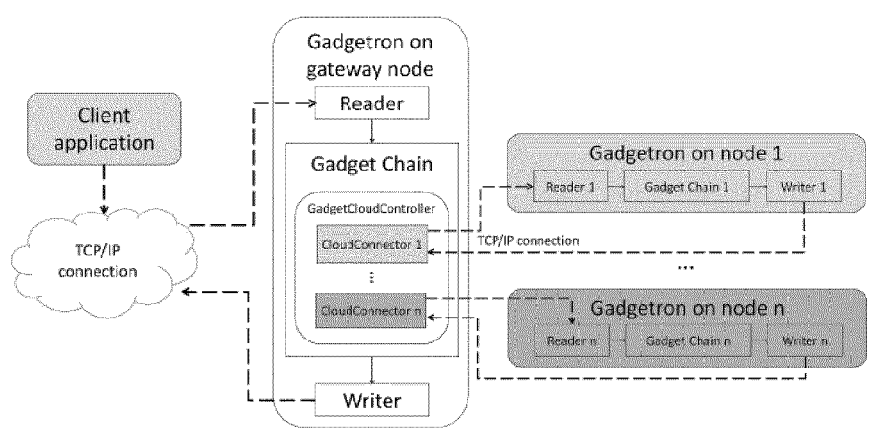
FIG. 2 depicts a presentation of GT-Plus distributed computing architecture for Gadgetron. In this example, at least one Gadgetron process is running on a node (Multiple Gadgetron processes can run in one node on different ports). The gateway node communicates with the client application (e.g. MRI scanner). It manages the connections to each of the computing nodes via the software module GadgetCloudController and GadgetronCloud Connector. Whenever sufficient data is buffered on the gateway node, the package can be sent to the computing node for processing Different computing nodes can run completely different reconstruction chain.

A schematic outline of GT-Plus extension is shown in FIG. 2. A distributed Gadgetron process has at least one Gadgetron running on a specific port for each node (multiple Gadgetron processes can run within the same node at different ports). A software module, GadgetCloudController, manages the communication between nodes. Typically, the gateway node is receiving the readout data from the client and de-serializes them using a Reader. Depending on the reconstruction workflow, the gateway node may buffer the incoming readouts and perform some processing before sending reconstruction jobs to the connected nodes, or data can be forwarded directly to the client nodes. The GadgetCloudController maintains multiple TCP/IP socket connections with every connected node via a set of GadgetronCloudConnector objects (one for each connected note). Each GadgetronCloudConnector has a reader thread (CloudReaderTask) and a writer thread (CloudWriterTask) which are responsible for receiving and sending data (to the node) respectively. There is a Gadgetron Gadget chain running on every connected node.

The gateway node will send the XML configuration to the connected node to assemble the chain. For different cloud nodes, different Gadget chains can be assembled. In fact, the connected nodes can also be gateway nodes, thus creating a multi-tiered cloud. The typical protocol of GT-Plus distributed computing is as follows:

a) The client issues the connection request to the GT-Plus gateway at a specific network port. Once the connection is established, the client will send the XML based configuration and parameter files to establish and initialize the gadget chain at the gateway node.
b) The client starts sending readout data to the gateway node.
c) The Gateway node establishes connection to cloud nodes and supplies them with XML configuration and parameter files. As mentioned, different connected nodes can be configured with different chains if needed.
d) Job packages are sent to connected cloud nodes for processing via the corresponding CloudWriterTask.
e) When all jobs are sent to nodes (the acquisition is done), the gateway Gadgetron either waits for reconstruction results or conducts extra computation. The ReaderTask objects, at the same time, listen for reconstruction results. Whenever the reconstruction results are sent back from a cloud node, the gateway Gadgetron is notified by the ReaderTask object and will take user-defined actions, e.g. passing the results downstream or waiting for the completion of all jobs. Finally the gateway node will proceed to finish other processing steps if any and send the images down the remaining part of the gateway Gadget chain and eventually back to the client.
f) If one or more connected nodes fail to complete a job successfully, the gateway node will be notified by either receiving an invalid result package or detecting a shutdown message on the socket. The GadgetCloudController on the gateway node will keep a record of uncompleted jobs and process them locally. In this way, the GT-Plus gains robustness against network instability.

The software modules mentioned above are implemented as C++ template classes and are capable of handling any type of custom job packages, i.e. the user is able to configure what data types are sent and received from the cloud nodes. The only requirement is to implement appropriate functions for serialization and de-serialization of work packages and results. This design is a straightforward extension of the Readers and Writers in the original Gadgetron.

In the current implementation, every computing node can be given an index indicating its computational power. This index is used to allow the gateway node to apply a scheduling algorithm where the workload is distributed to the cloud nodes in proportion to their computational capabilities. This can be important if the cloud consists of a heterogeneous set of hardware configuration.

To supply the network connection information of cloud nodes to the Gadgetron, user can specify IP addresses or hostnames of nodes in the gateway XML configuration file. Alternatively, the framework can read in a cloud structure definition file.

Gadgetron Plus (GT-Plus) for 2D Time Resolved (2D+t) Reconstruction Tasks

Figure 3:
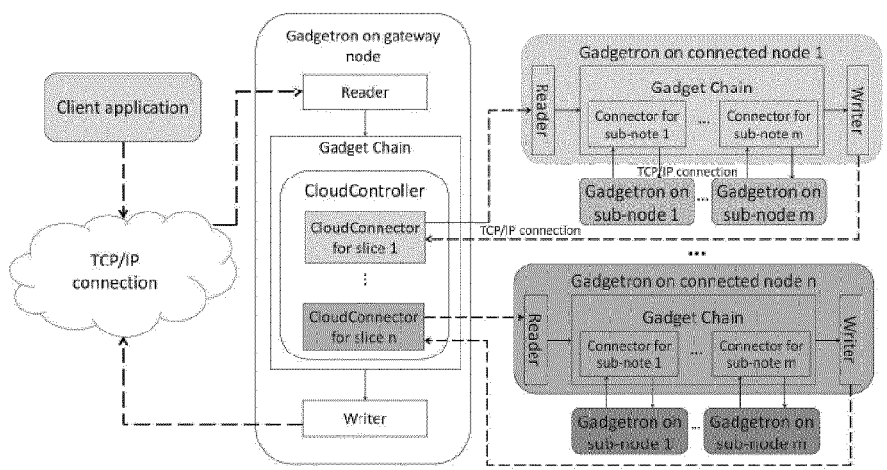
FIG. 3 depicts a dual-layer topology of cloud computing for 2D+t applications. Every connected node contains its own GadgetCloudController and can split a reconstruction task for a slice to its sub-nodes. Compared to the basic cloud topology shown in FIG. 2, this dual layer example adds extra complexity. This example demonstrates the flexibility of GT-Plus architecture for composing different computing cloud topology to fit different reconstruction tasks.

In addition to the software modules for cloud communication, the GT-Plus extensions also include a specific job type to support 2D+t reconstruction tasks, e.g. multi-slice cine imaging. This workflow is used here to illustrate a cloud setup with a dual layer topology, as illustrated in FIG. 3. The gateway gadget chain will buffer readouts for a specified ISMRMRD dimension (e.g. for the multi-slice cine, it is usually the slice dimension). Once all data for a slice have arrived, the GtPlusRecon2DTGadgetCloud gadget will forward the job package to a first layer node to start the reconstruction.

For a 2D+t dynamic imaging task, one slice will have multiple 2D k-spaces. For example, for the cardiac cine acquisition, multiple cardiac phases are usually acquired. The first layer node responsible for the reconstruction of a given slice can choose to further distribute the dataset to a set of sub-nodes in the second layer. The first-layer nodes can serve solely to distribute jobs or they can perform computation as well. In principle, a given reconstruction job can utilize an arbitrary number of node layers to form a more complicated cloud topology.

Gadgetron Plus (GT-Plus) for 3D Reconstruction Tasks

For 3D acquisitions, a single layer cloud topology was used in this paper. The gateway node's GtPlusRecon3DTGadget receives the 3D acquisition and performs the processing such as coil compression and estimation of k-space convolution kernel for parallel imaging. It then splits the large 3D reconstruction problem by performing a 1D inverse FFT transform along the readout direction. Thus, the reconstruction is decoupled along the readout direction. Every chunk of data along the readout direction is then sent to a connect node for non-linear reconstruction. The gateway node will wait for all jobs to complete and results to return. It then reassembles the 3D volume from all chunks and continues to perform other post-processing, e.g. k-space filtering tasks and finally returns images to the client.

Toolbox Features

The Gadgetron is divided into Gadgets and Toolbox algorithms that can be called from the Gadgets or standalone applications. In addition to the toolbox features listed in (15), the GT-Plus extensions add additional toolboxes. Here is an incomplete list of key algorithm modules:

2D/3D GRAPPA.

A GRAPPA implementation for 2D and 3D acquisition is added. It fully supports the ISMRMRD data format and different parallel imaging modes (embedded, separate or interleaved auto-calibration lines, as defined in (19)). For the 3D GRAPPA case, the implementation supports two-dimensional acceleration. To support parallel imaging in interactive or real-time applications, a real-time high-throughput 2D GRAPPA implementation using GPU is also provided in the Gadgetron.

2D/3D Linear SPIRiT.

A linear SPIRiT (7) reconstruction is implemented in the Gadgetron toolbox. Specifically, if the k-space x consists of filled points a and missing points m, then:

$$x = D^T a + D_c^T m \quad (1)$$

Here x is an vector containing k-space points for all phase encoding lines for all channels; a stores the acquired points, and m is for missing points. D and $D_c$ are the sampling pattern matrixes for acquired and missing points, Linear SPIRiT solves the following equation:

$$(G-I)D_c^T m = (G-I)D^T a \quad (2)$$

Here G is the SPIRiT kernel matrix, which is computed from a fully sampled set of auto calibration data.

2D/3D Non-linear l1-SPIRiT.

Equation 2 is extended by the L1 term:

$$\operatorname{argmin}_m \{\|(G-I)(D^T a + D_c^T m)\|_2 + \lambda \|W\Psi C^H F^H (D^T a + D_c^T m)\|_1\} \quad (3)$$

Another variation of l1SPIRiT is to treat the full k-space as the unknowns:

$$\operatorname{argmin}_x \{\|(G-I)x\|_2 + \lambda \|W\Psi C^H F^H x\|_1 + \beta \|Dx - a\|_2\} \quad (4)$$

Here Ψ is the sparse transform and W is an extra weighting matrix applied on the computed sparse coefficients to compensate for non-isotropic resolution or temporal redundancy. F is the Fourier transform matrix. C is the coil sensitivity.

Redundant 2D and 3D Wavelet Transform.

The redundant wavelet transform for 2D and 3D data arrays are implemented in the toolbox. It is used in the L1 regularization term. A fast implementation for redundant Harr wavelet is also provided.

Example Applications

Corresponding to the two types of cloud topologies described in the previous sections, two in vivo experiments were performed on healthy volunteers. The local Institutional Review Board approved the study, and all volunteers gave written informed consent.

Real-Time Multi-Slice Myocardial Cine Imaging Using l1-SPIRiT

The aim was to make it clinically feasible to assess myocardial function using real-time acquisitions and non-linear reconstructions covering the entire ventricles. With conventional reconstruction hardware, the reconstruction time for such an application would prohibit clinical adoption. The dual layer cloud topology was used here and every slice was sent a separate node (first layer) which further split cardiac phases into multiple chunks. While processing one chunk itself, the first layer node also sent others to its sub-nodes for parallel processing. The algorithm workflow was as follows: a) Undersampled k-space data were acquired with the time-interleaved sampling pattern. b) The gateway node received the readout data and performed the on-the-fly noise pre-whitening (5). c) The data from one slice was sent to one first layer node. d) To reconstruct the underlying real-time cine images, the auto-calibration signal (ACS) data for a slice were obtained by averaging all undersampled k-space frames at this slice. e) The SPIRiT kernel was estimated on the assembled ACS data. f) The data for the slice was split into multiple chunks and sent to sub-nodes, together with the estimated kernel. The size of a data chunk for a node was proportional to its computing power index. f) Sub-nodes received the data package and solved equation 3. The linear SPIRiT problem (equation 2) was first solved to initialize the non-linear solver. g) Once the process for a slice was completed, the node sent the reconstructed frames back to gateway, which then returned them to the scanner. Note the reconstruction for a given slice started while acquisition was still ongoing for subsequent slices. Thus the data acquisition and processing was overlapped in time to minimize the overall waiting time after the data acquisition.

Figure 4:
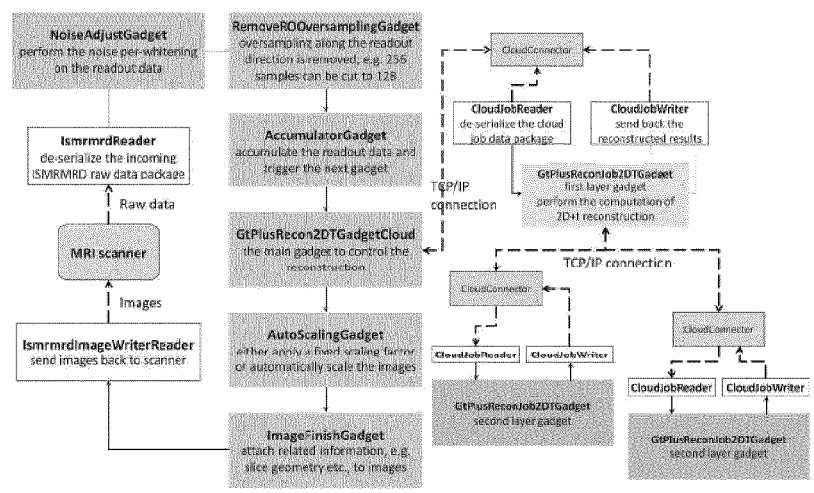
FIG. 4 depicts the gadget chain used in the multi-slice myocardial cine imaging. Here the GtPlusRecon2DTGadgetCloud gadget controls the connection to the first layer node where the data from a slice was reconstructed. The second layer sub-nodes were further utilized to speed up the reconstruction. The TCT/IP socket connections were established and managed by the cloud software module implemented in the GT-Plus.

FIG. 4 outlines the l1SPIRiT reconstruction gadget chain for multi-slice cine imaging using the dual layer cloud topology. The raw data first went through the NoiseAdjustGadget, which performed noise pre-whitening. After removing the oversampling along the readout direction, the data was buffered in the AccumulatorGadget. Whenever the acquisition for a slice was complete, the data package was sent to the GtPlusRecon2DTGadgetCloud gadget, which established the network connection to the first layer nodes and sent the data.

The first layer node ran only the GtPlusReconJob2DTGadget gadget, which then connected to the second layer nodes. The CloudJobReader and CloudJobWriter were used to serialize and de-serialize the cloud job package.

Imaging experiments were performed on a 1.5T clinical MRI system (MAGNETOM Area, Siemens AG Healthcare Sector, Erlangen, Germany) equipped with a 32-channel surface coil. A healthy volunteer (female, 23.8 yrs) was scanned. Acquisition parameters for free-breathing cine were as follows: balanced SSFP readout, TR=2.53/TE=1.04 ms, acquired matrix size 192×100, flip angle 60°, FOV 320×240 mm², slice thickness 8 mm with a gap of 2 mm, bandwidth 723 Hz/pixel, interleaved acquisition pattern with acceleration factor R=5. The whole left ventricular was covered by 9 slices and acquisition duration for every slice was ~1.5 s with one dummy heartbeat between slices. The scan time (defined as the time to perform data acquisition) to complete all 9 slices was 22.6 s.

High Resolution Neuro Imaging Using l1-SPIRiT

The second example aimed to use GT-Plus for non-linear reconstruction of a high resolution 3D acquisition. The algorithm workflow was as follows: a) Undersampled k-space data were acquired with the fully sampled center region. b) The gateway node received the readout data and performed the on-the-fly noise pre-whitening. c) When all data was received, the SPIRiT kernel calibration was performed on the fully sampled ACS region. The kernel was zero-padded only along the readout direction and Fourier transformed to the image domain. This was done to reduce the maximal memory needed to store the image domain kernel and decrease the amount of data transferred over the network to connected nodes. The k-space data was transformed to image domain along the readout as well. d) The gateway node split the image domain kernel and data into multiple chunks along the readout direction and sent them to multiple connected nodes. e) The connected nodes received the packages and zero-padded kernels along the remaining two spatial dimensions and transformed into image domain. The image domain kernel was applied to the aliased images by pixel-wise multiplication. This linear reconstruction was performed to initialize the non-linear reconstruction. f) After receiving all reconstructed image from connected nodes, the gateway assembled the 3D volume and performed post-processing, such as k-space filtering and then sent results back to the scanner.

The imaging experiments were performed on a 3.0T clinical MRI system (MAGNETOM Skyra, Siemens AG Healthcare Sector, Erlangen, Germany) equipped with a 20-channel head coil. The acquisition parameters were as follows: GRE readout, TR=10.0/TE=3.11 ms, acquired matrix size 256×256×192, flip angle 20°, isotropic spatial resolution 1 mm³, bandwidth 130 Hz/pixel, two dimension acceleration factor R=3×2. The embedded parallel imaging mode was used with the ACS signal acquired as a 32×32 fully sampled region. The total acquisition time was 91.6 s.

Deployment and Scanner Integration

The cloud extension of Gadgetron (GT-Plus), can be deployed on different types of platforms. Three setups have been tested here for in vivo experiments and the GT-Plus software can be deployed on those setups without any code changes. The first setup (referred to as the "casual cloud") is a heterogeneous collection of computers, e.g. as one would find in many MRI research laboratories. These computers have different hardware and operating system configurations. The second setup is the NIH Biowulf cluster, which is a custom built cluster with totally 2300 nodes (>12000 computing cores); it is a shared system and users request a specific amount of resources for a given computational task. The third setup is the Amazon Elastic Compute Cloud (EC2), where an arbitrary amount of computational power can be rented by the hour providing the flexibility to tailor the cloud configuration to suit a specific application.

"Casual" Cloud

The first setup is a solution that almost any MRI research laboratory would be able to use by installing the Gadgetron on a set of networked computers and using one of these computers as the gateway node. No specific operating system or special hardware is needed. Here, six personal computers on the NIH intranet (1 Gb/s connections) were used as the cloud nodes and two more computers were used as gateway nodes for 2D+t and 3D experiments respectively. The Gadgetron software was compiled and installed on all computers. The gateway node for 2D+t test was a desktop computer, running windows 7 Pro 64 bit (four core Intel Xeon E5-2670 2.60 GHz processors, 48 GB DDR3 RAM). The gateway node for 3D test also ran the same operating-system (two eight-core Intel Xeon E5-2670 2.60 GHz processers, 192 GB DDR3 RAM).

Among the six cloud nodes, two of them were running windows 7 Pro 64 bit (each had four cores of Intel Xeon E5-2670 2.60 GHz, and 48 GB DDR3 RAM). Ubuntu linux 12.04 were running on other four nodes (two nodes each had six cores of Intel Xeon E5645 2.4 GHz and 24 GB DDR3 RAM; the other two had four cores of Intel Xeon X5550 2.67 GHz and 24 GB DDR3 RAM).

For the dual layer cloud test, one Windows and two Ubuntu computers served as first layer nodes. The other three nodes were on the second layer. Each of them was connected to one first layer node. For the 3D reconstruction test, all six nodes were connected directly to the gateway.

NIH Biowulf Cloud

The second cloud setup tested in this study utilized the NIH Biowulf cluster. NIH Biowulf system is a GNU/Linux parallel processing system designed and built at the National Institutes of Health. Biowulf consists of a main login node and a large number of computing nodes. The computing nodes within Biowulf are connected by a 1 Gb/network. The MRI scanner used in this study was also connected to Biowulf system with a 1 Gb/s network connection. For the 2D multi-slice cine experiments 37 nodes were requested from the cluster. The gateway node had 16 cores (two eight-core Intel Xeon E5-2670 2.60 GHz processors) and 72 GB DDR3 RAM. All other nodes had identical configurations (two six-core Intel Xeon X5660 2.80 GHz, 24 GB DDR3 RAM). For the dual layer cloud test, 9 nodes were used on the first layer to match the number of acquired slices. Each of them was connected to three sub-nodes on the second layer. For the 3D reconstruction test, the same gateway node and 23 connected nodes were requested.

The cloud topology was selected to balance the maximal parallelization and programming complexity. It is convenient to have dual layer structure for the multi-slice cine imaging, because this structure allows overlap between data acquisition and reconstruction computation. For the 3D acquisition, the reconstruction only starts when the data acquisition is completed; therefore, a simple one layer cloud is used to simplify the synchronization. The number of nodes used in the study was mainly limited by the available resources during the experiments. Although Biowulf system has a large number of nodes, hundreds of jobs from multiple users can run in parallel at any given time. We also intentionally made number of nodes different between 2D+t and 3D tests, to challenge the scalability of Gadgetron based cloud software.

Amazon EC2 Based Cloud

The last setup utilized the Amazon Elastic Compute Cloud (Amazon EC2). Amazon EC2 cloud provides resizable computing capacity in the Amazon Web Services (AWS) cloud. User can configure and launch flexible number of computing nodes. Every node can have different hardware configuration and operating system. Amazon EC2 provides a broad selection of Windows and Linux operating systems. More details about Amazon EC2 can be found in (21).

For this study, 19 nodes were launched to build up a virtual cloud on Amazon EC2. Every node used the cc2.8× large instance type (two eight-core Intel Xeon E5-2670 2.60 GHz processors, 20 MB L3 cache per processor, 60 GB DDR3 RAM), running Ubuntu Server 13.10. All nodes were connected 10 Gb/s connections. For the dual layer test, one node was used as the gateway and 9 nodes were on the first layer. Each first layer nodes were connected to two other sub-nodes. Thus, data for every slice was processed by three nodes in total. For the 3D reconstruction test, all 18 nodes are connected directly to the gateway. At the time of the study, the price for the nodes used in this test was US $2.4 per hour per node or US $45.60 per hour for the complete cloud setup. In this case, the number of nodes was chosen as a reasonable balance between cost and performance.

The connection speed from the MRI scanner to the Amazon EC2 cloud was measured to be 49.8 MB/s or 0.39 Gb/s at the time of the experiments.

Clinical Scanner Integration

As previously described, the Gadgetron enables direct integration with the MRI scanner for online reconstruction (15). The cloud extension of GT-Plus maintains this advantage of online processing. Effectively, this setup enables a seamless connection of cloud computing resources directly to the scanner. From the end-user perspective, the only noticeable difference between reconstruction in the cloud and locally (on the scanner's reconstruction hardware) is the improvement in reconstruction speed.

The integration of cloud computing resources with a clinical scanner raises questions about patient privacy. In this study multiple steps were taken to mitigate any risks. Firstly, all data being sent to the Gadgetron from the scanner was anonymized. Absolutely no identifying information that could be used to trace back to the patient were sent over the network. The only information sent was the MR raw data and protocol parameters such as field of view, matrix size, bandwidth, etc. Secondly, all data transfer between scanner and gateway node was encrypted via a secure shell (SSH) tunnel (24). All other nodes connected to the gateway were behind firewalls. Besides serving as a security measure, the use of SSH tunnels to connect to the Gadgetron was a convenient way to test multiple Gadgetron setups on the same scanner. The reconstruction could simply be directed to a different Gadgetron by changing the SSH tunnel pointing to a different Gadgetron instance.

Tests were performed on two clinical MRI scanners (Siemens Skyra 3.0T and Area 1.5T, Siemens Medical Solutions, Erlangen, Germany).

Results

Multi-Slice Myocardial Cine Imaging

Figure 5:
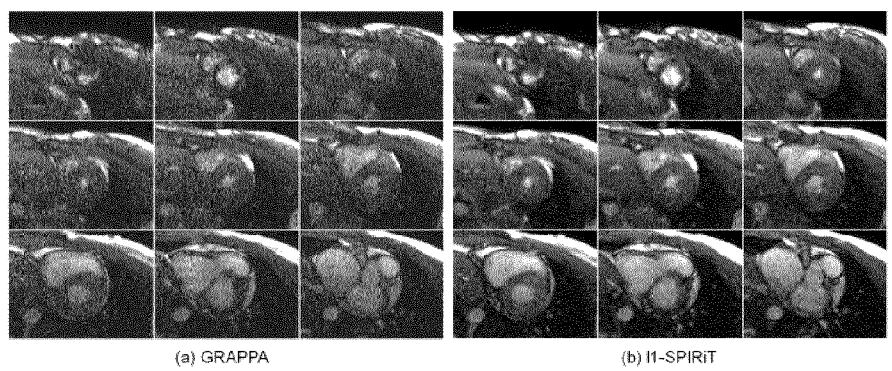
FIG. 5 depicts the reconstruction results of multi-slice myocardial cine imaging on the GT-Plus cloud. Compared to the linear reconstruction (a), non-linear reconstruction (b) improves the image quality. With the computational power of Gadgetron based cloud, the entire imaging including data acquisition and non-linear reconstruction can be completed in 1 min to achieve the whole heart coverage.

FIG. 5 shows the reconstruction results generated by the GT-Plus cloud, illustrating the noticeable improved in image quality using non-linear reconstruction.

Table 1 shows the total imaging time and computing time. The imaging time is the time period from the start of data acquisition to the moment when images of all slices were returned to scanner. The computing time is defined as the time used to perform the reconstruction computation. On the described Amazon EC2 cloud, the total imaging time was 52.6 s. The computing time was 48.9 s because the computation was overlapped with the data acquisition. On the NIH's Biowulf cloud, imaging and computing times were 62.1 s and 58.2 s respectively. If only a single node was used, the computing time was 427.9 s and 558.1 s for two cloud setups. Therefore, the multi-slice cine imaging with entire ventricle coverage was completed within 1 min using the non-linear reconstruction on the GT-Plus cloud. The casual cloud gave computing time of 255.0 s and if only one node was used, the time went up to 823.7 s. This speedup may be helpful to the development and validation of non-linear reconstruction in a MRI research lab.

High Resolution 3D Neuroimaging

Figure 6:
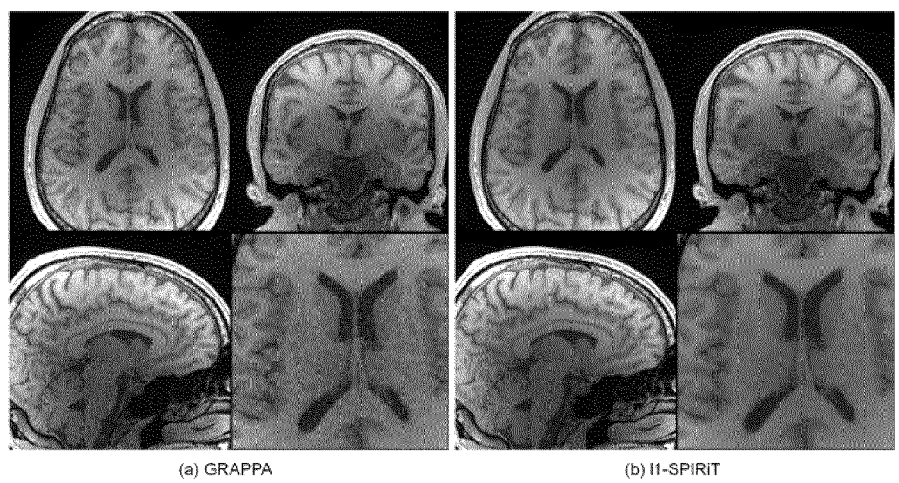
FIG. 6 depicts reconstruction results of 1 $mm^3$ brain acquisition on the GT-Plus cloud. The basic cloud topology shown in FIG. 2 was used here. Both GRAPPA linear reconstruction (a) and (the l1SPIRIT results (b) are shown here. The single node processing time is over 20 mins, which prohibits the clinical usage of non-linear reconstruction. With the Gadgetron based cloud, a computing time of <2.5 mins can be achieved for this high resolution acquisition.

FIG. 6 illustrates the cloud reconstruction results using l1-SPIRiT. Compared to the GRAPPA, the non-linear reconstruction shows noticeable SNR improvements. Table 2 gives the total imaging time and computing time for three cloud setups and the single node processing. The total imaging time on the Biowulf cloud was 278.5 s which includes the computing time of 186.4 s, since not all computational steps ran in parallel for this 3D reconstruction. As every computing node of the Amazon EC2 cloud setup had 16 cores and a newer CPU model, the total computing time was further reduced to 146.0 s. Total imaging time on the Amazon cloud was 255.0 s. Thus the latency following data acquisition was less than 2 mins.

Availability and Platform Support

The entire package is integrated with the currently available version of the Gadgetron, which is distributed under a permissive, free software license based on the Berkeley Software Distribution license. The licensing terms allow users to use, distribute and modify the software in source or binary form. The source code. The documentation can be found at the Sourceforge Open Source distribution website for Gadgetron (http://gadgetron.sourceforge.net/). The software has been compiled and tested on Microsoft Windows 7 64 bit, Ubuntu Linux, CentOS 6.4, and Mac OS X (Note this paper does not present examples running on CentOS and Mac OS X, but the software has been compiled and tested on those two operating systems).

Discussion

This work extends the previously published Gadgetron framework to support distributed computing, which makes it possible to distribute a demanding reconstruction task over multiple computing nodes and significantly reduce the processing time. This paper focused on reducing the processing time of non-linear reconstruction applications, which have so far been difficult to deploy clinically. As demonstrated in the examples, the increased computational power could make the processing time of non-linear reconstruction feasible for the regular clinical use.

The Gadgetron Plus (GT-Plus) extension provides a set of utility functions to manage and communicate with multiple nodes. Based on these functions, flexible cloud topologies can be realized as demonstrated in this paper. In the current Gadgetron software release, the discussed dual-layer and single layer cloud implementation are made available to the community. They are designed and implemented for general-purpose use, although the examples given are specific for cine and 3D neuroimaging. Based on the GT-Plus extensions new cloud topologies will be explored in the future and users can design and implement their own cloud structure.

The Gadgetron based cloud computing was deployed on three different types of cloud computing hardware. This demonstrates the flexibility both Gadgetron framework in general and the GT-Plus extensions specifically. The casual cloud setup is the cheapest, most accessible way of using Gadgetron cloud computing. It can be set up quickly and used for algorithm development and validation in a research laboratory. The disadvantage of using such a setup is the computing nodes may be very heterogeneous and optimal distribution of the work among nodes may become non-trivial. If cloud computing is used in a production type setting on a clinical scanner, it is also problematic that a node may be busy with other tasks when it is needed by the scanner.

The Amazon EC2 system, on the other hand, provides a professional grade cloud setup with 24/7 availability. The computational resources can be dedicated for a specific project or scanner and the nodes can in general have the same configuration, which reduces the complexity of scheduling. This setup is also easy to replicate and share among groups and scanners. There are other companies that provide the same type of cloud infrastructure service, e.g. Rackspace (http://www.rackspace.com/). With these vendors the users pay by hour to rent computers. In the setup we describe in this paper, the cost of running the cloud was on the order of US $50 per hour. While this cost could be prohibitive if the cloud is enabled 24 hours per day, it is a relatively modest cost in comparison to the cost typical patient scans. Moreover, this cost is falling rapidly with more service providers entering into the market and more powerful computing hardware becoming available. The main downside of using a remote cloud service such as Amazon EC2 is the need for a high-speed Internet connection to the cloud provider. At large universities 1 Gb/s connections (which are sufficient for the applications presented here) are becoming commonplace. However, this may not be the case for hospitals in general.

The third setup, the NIH's Biowulf, is a dedicated, custom built, cluster system. While not available to the entire MRI community, it represents a parallel computing platform often found at research institutions (such as universities) or large corporations. For large organizations aiming to provide imaging, reconstruction and processing service for a large number of scanners, this setup may be the most cost effective platform. It is, however, important to note that purchasing, configuration, deployment, and management of even modest cloud computing resources is a non-trivial task that requires significant resources.

Several software modules implemented in the Gadgetron framework are GPU accelerated, although the demonstrated examples in this paper are mainly using CPUs. The GT-Plus extension of distributed computing does not conflict with GPU based computational acceleration in any sense. Every computing node can be equipped with different hardware; for those with good GPU processers or CPU coprocessors (e.g. Intel Xeon Phi coprocessors http://www.intel.com/content/www/us/en/processors/xeon/xeon-phi-detail.html), the local processing can utilize those resources, since the Gadgetron framework allows every node to be configured with different Gadget chains. Heterogeneous computational hardware across nodes can be challenging for optimal load balancing. In the current framework, the user can supply computing power indexes for nodes to indicate its strength. But the framework does not presently implement more complicated approaches to help determine the computing ability of every node.

The Gadgetron framework and its toolboxes are mainly programmed using C++ and fully utilize generic template programming. While efforts are made to provide documentation and examples in the Gadgetron distribution, developers who want to extend the toolboxes still need some proficiency with object oriented programming and C++ in particular.

Conclusion

We have developed the Gadgetron Plus extension for the Gadgetron framework to support distributed computing using various cloud setups. We have deployed the Gadgetron based distributed computing over three very different cloud environments. We have shown the increased computational power in the cloud significantly speeds up l1-SPIRIT reconstruction for 2D+t dynamic imaging and high-resolution 3D acquisitions.

REFERENCES

1. Blaimer M, Breuer F, Mueller M, Heidemann R M, Griswold M A, Jakob P M. SMASH, SENSE, PILS, GRAPPA: How to Choose the Optimal Method. Topics in Magnetic Resonance Imaging 2004; 15(4):223-236.
2. Breuer F A, Kellman P, Griswold M A, Jakob P M. Dynamic autocalibrated parallel imaging using temporal GRAPPA (TGRAPPA). Magnetic Resonance in Medicine 2005; 53(4):981-985.
3. Griswold M A, Jakob P M, Heidemann R M, Nittka M, Jellus V, Wang J, Kiefer B, Haase A. Generalized autocalibrating partially parallel acquisitions (GRAPPA). Magnetic Resonance in Medicine 2002; 47(6):1202-1210.
4. Kellman P, Epstein F H, McVeigh E R. Adaptive sensitivity encoding incorporating temporal filtering (TSENSE). Magnetic Resonance in Medicine 2001; 45(5):846-852.
5. Pruessmann K P, Weiger M, Scheidegger M B, Boesiger P. SENSE: Sensitivity encoding for fast MRI. Magnetic Resonance in Medicine 1999; 42(5):952-962.
6. Lustig M, Donoho D, Pauly J M. Sparse MRI: The application of compressed sensing for rapid MR imaging. Magnetic Resonance in Medicine 2007; 58(6):1182-1195.
7. Lustig M, Pauly J M. SPIRIT: Iterative self-consistent parallel imaging reconstruction from arbitrary k-space. Magnetic Resonance in Medicine 2010; 64(2):457-471.
8. Hansen M S, Atkinson D, Sorensen T S. Cartesian SENSE and k-t SENSE reconstruction using commodity graphics hardware. Magnetic Resonance in Medicine 2008; 59(3):463-468.
9. Sorensen T S, Schaeffter T, Noe K O, Hansen M S. Accelerating the Nonequispaced Fast Fourier Transform on Commodity Graphics Hardware. Medical Imaging, IEEE Transactions on 2008; 27(4):538-547.
10. Jung H, Sung K, Nayak K S, Kim E Y, Ye J C. k-t FOCUSS: A general compressed sensing framework for high resolution dynamic MRI. Magnetic Resonance in Medicine 2009; 61(1):103-116.
11. Liang D, DiBella E V R, Chen R-R, Ying L. k-t ISD: Dynamic cardiac MR imaging using compressed sensing with iterative support detection. Magnetic Resonance in Medicine 2011; 68(1):41-53.
12. Lustig M, Santos J M, Donoho D L, Pauly J M. k-t SPARSE: High Frame Rate Dynamic MRI Exploiting Spatio-Temporal Sparsity. 2006 6-12 May; Seattle, Wash., USA. p 2420.
13. Vasanawala S S, Alley M T, Hargreaves B A, Barth R A, Pauly J M, Lustig M. Improved Pediatric MR Imaging with Compressed Sensing. Radiology 2010; 256(2):607-616.
14. Vasanawala S S, Murphy M J, Alley M T, Lai P, Keutzer K, Pauly J M, Lustig M. Practical parallel imaging compressed sensing MRI: Summary of two years of experience in accelerating body MRI of pediatric patients. 2011 Mar. 30-Apr. 2; Chicago, Ill. p 1039-1043.
15. Hansen M S, Sørensen T S. Gadgetron: An open source framework for medical image reconstruction. Magnetic Resonance in Medicine 2012; 69(6):1768-1776.
16. Feng Y, Song Y, Wang C, Xin X, Feng Q, Chen W. Fast direct fourier reconstruction of radial and PROPELLER MRI data using the chirp transform algorithm on graphics hardware. Magnetic Resonance in Medicine 2013; 70(4):1087-1094.
17. Simpson R, Keegan J, Gatehouse P, Hansen M, Firmin D. Spiral tissue phase velocity mapping in a breath-hold with non-cartesian SENSE. Magnetic Resonance in Medicine 2013:doi: 10.1002/mrm.24971.
18. Xue H, Kellman P, LaRocca G, Arai A, Hansen M. High spatial and temporal resolution retrospective cine cardiovascular magnetic resonance from shortened free breathing real-time acquisitions. Journal of Cardiovascular Magnetic Resonance 2013; 15:102.
19. Hansen M S. Sharing Reconstruction Software—Raw Data Format and Gadgetron. 2013; Sedona, Ariz., USA.
20. NIH Biowulf cluster system. http://biowulf.nih.gov/. Bethesda, Md., USA. Jul. 15, 2013.
21. Amazon Elastic Compute Cloud (Amazon EC2). http://aws.amazon.com/ec2/. Jul. 12, 2013.
22. Schmidt D C. The ADAPTIVE communication environment: object-Oriented Network Programming Components for Developing Client/Server Applications. The 11th Annual Sun Users Group Conference. San Jose, Calif., USA 1993. p 214-225.
23. Lavender R G, Schmidt D C. Active object: an object behavioral pattern for concurrent programming. In: John M V, James O C, Norman L K, editors. Pattern languages of program design 2: Addison-Wesley Longman Publishing Co., Inc.; 1996. p 483-499.
24. Network Working Group of the IETF. The Secure Shell (SSH) Authentication Protocol. 2006.

TABLE 1

Total imaging time (from the start of data acquisition to the moment when all images are returned to the scanner) and computing time in seconds for the multi-slice myocardial cine imaging. The in vivo test was only performed with cloud setups. The single node computing time was recorded with the retrospective reconstruction on the gate-way node.

|  | Casual | | Biowulf | | Amazon E C2 | |
| --- | --- | --- | --- | --- | --- | --- |
|  | Single | Cloud | Single | Cloud | Single | Cloud |
| Imaging time (s) | — | 259.2 | — | 62.1 | — | 52.6 |
| Computing time (s) | 823.7 | 255.0 | 558.1 | 58.2 | 427.9 | 48.9 |

TABLE 2

Total imaging and computing time in seconds for the 3D neuro acquisition. The single node used for comparison is the gateway node for every cloud setup.

|  | Casual | | Biowulf | | Amazon EC2 | |
| --- | --- | --- | --- | --- | --- | --- |
|  | Single | Cloud | Single | Cloud | Single | Cloud |
| Imaging time (s) | — | 541.9 | — | 278.5 | — | 255.0 |
| Computing time (s) | 1054.3 | 449.1 | 1265.1 | 186.4 | 983.5 | 146.0 |

EXAMPLE 2

3D High Resolution 11-Spirit Reconstruction on Gadgetron Based Cloud

Introduction

Non-linear and iterative reconstruction algorithms have been the subject of intense study in the MR imaging community. Very promising algorithms have been published in the literature, including image domain compressive sensing [1] and k-space SPIRiT and its regularized versions [2]. Given the lengthy acquisition time of high resolution 3D MRI imaging, it is of great interest to apply non-linear reconstruction to shorten the imaging. The robustness against subject movement or uncooperative pediatric patients can be improved. However, the clinical usage of these techniques is often prohibited by the high demand for computational power and very long reconstruction time. To achieve practical reconstruction times for clinical usage of non-linear reconstruction, we have extended the previously published Gadgetron framework [3] to support the distributed computing across multiple computers. This extension is named "Gadgetron Plus" or "GT-Plus". A cloud version of 3D 11-SPIRiT reconstruction was implemented on the GT-Plus cloud framework and applied to high-resolution 3D neuroimaging. With the use of the computational power of the cloud, we demonstrate that a 3 mins reconstruction can be achieved for 1 $mm^3$ isotropic neuro scans using 11-SPIRiT. Compared to the linear reconstruction, the image quality was significantly improved.

Architecture and Implementation

At least one Gadgetron process was started at every node. The inter-node communication was managed by a software module GadgetCloudController using TCP/IP sockets. A gateway node was connected to the scanner and received readout data. It then sent buffered data package to computing nodes for processing. Every computing node was responsible for processing the received job via its processing chain and forwarded results back to the gateway. With all expected results received on the gateway, images were be sent back to the scanner.

Cloud version of 3D L1SPIRiT

The gateway node was configured to receive the readouts for a 3D acquisition and perform k-space convolution kernel estimation. It then split the large 3D reconstruction problem by performing the 1D inverse FFT transform along the readout direction. Thus, the reconstruction was decoupled along the readout direction. Every chunk of data along the readout direction was sent to one computing node. The L1SPIRiT algorithm was running on every node. The redundant Harr wavelet transform was used in the regularization term.

Deployment on Cloud Systems

Two cloud setups were tested. Amazon EC2 based cloud 19 nodes were launched on the Amazon Elastic Compute Cloud (Amazon EC2). All nodes had two eight-core Intel Xeon E5-2670 2.60 GHz processors, running Ubuntu Server 13.10. The gateway node had 240 GB RAM and others had 60 GB. NIH Biowulf cluster 23 nodes were requested from the Biowulf cloud (http://biowulf.nih.gov) which is a linux based parallel computing system (Red Hat Server 5.10) and built at National Institutes of Health, USA. The gateway node had 16 CPU cores (two eight-core Intel Xeon E5-2670 2.60 GHz processors) and 256 GB RAM. All other nodes had two six-core Intel Xeon X5660 2.80 GHz processors and 24 GB RAM. For both cloud setups, "online" reconstruction was achieved. That is, the acquired readout data was sent to cloud while the scan was proceeding. The reconstructed images were directly sent back to the scanner and stored in the clinical PACS.

In-Vivo test Cloud based reconstruction was performed for high resolution neuro acquisition. A healthy volunteer was scanned on a 3.0T clinical MRI system (MAGNETOM Skyra, Siemens, 20-channel head coil). Acquisition parameters were: GRE readout, TR=7.0/TE=3.07 ms, acquired matrix size 256×256×192, flip angle 20°, 1 $mm^3$ isotropic spatial resolution, bandwidth 120 Hz/pixel, two dimension acceleration R=3×2 and 3×3 with a 32×32 fully sampled k-space center. The total acquisition time was 65 s and 46 s for two acceleration levels.

Results

Figure 7:
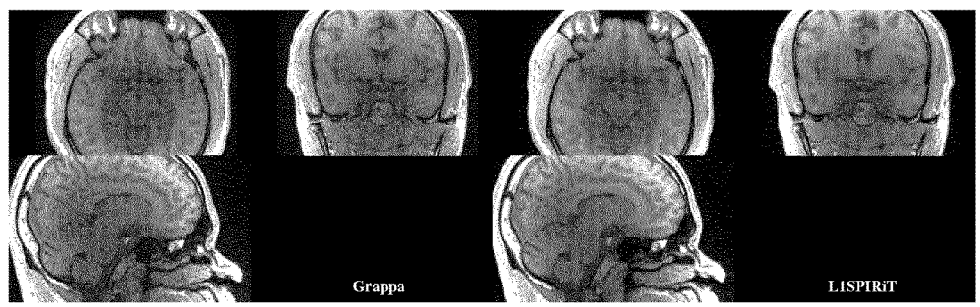
FIG. 7 depicts reconstruction results of 3D neuro scan on the GT-Plus cloud for two-dimensional acceleration R=3×2. Compared to the Grappa linear reconstruction on the left, non-linear reconstruction on the right gives noticeable improvement in signal to noise. For this 1 $mm^3$ protocol, the cloud version of non-linear reconstruction was completed within 3 mins after the end of data acquisition, while on a single-node reconstruction took >15 mins. This reduction of computing time could be crucial for clinical usage of advanced image reconstruction techniques.
Figure 8:
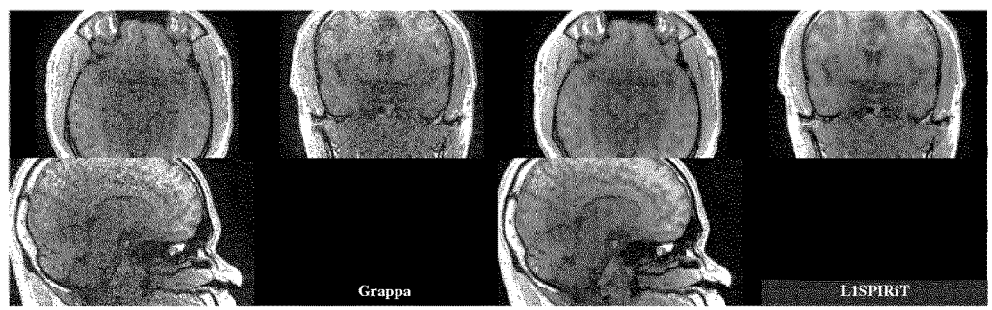
FIG. 8 depicts reconstruction results of 3D neuro scan on the GT-Plus cloud for two-dimensional acceleration R=3×3. Compared to the Grappa linear reconstruction shown on the left and results shown in FIG. 7, the improvement in image quality is even more substantial for higher acceleration. Since the head coil used for this test has 20 channels, the R=3×3 acceleration severely degrades the Grappa reconstruction because of the elevated g-factor, while l1-SPIRiT reconstruction is much more robust in this case.

FIG. 7 shows the reconstruction results generated on the GT-Plus based cloud for R=3×2. FIG. 8 is for R=3×3. Both cases indicate non-linear reconstruction noticeably improved image quality, compared to the linear GRAPPA reconstruction. The reconstruction time (defined as the computing time to perform the reconstruction algorithms) was 171 s for R=3×2 and 170 s for R=3×3 on the described Amazon EC2 cloud. On the Biowulf system, the reconstruction time was 239 s and 242 s. If only a single node was used, much longer reconstruction time was experienced: for R=3×2 and 3×3, the Amazon EC2 cloud recorded 1002 s and 1022 s and for the Biowulf system, computation took 1279 s and 1338 s respectively.

Conclusions

The GT-Plus extension for Gadgetron framework was developed to support distributed computing across multiple nodes. The 3D 11-SPIRiT algorithm was implemented on the Gadgetron based cloud, giving significantly reduced reconstruction time for high resolution neuro scans. This speedup can enable the clinical usage of advanced non-linear reconstruction algorithms on 3D MR applications.

REFERENCES

[1] Lustig M, et al., MRM 58:1182-1195
[2] Lustig M, et al., MRM 64:457-471
[3] Hansen M S, et al., MRM 69:1768-1776 (2013)

EXAMPLE 3

Distributed Computing on Gadgetron: A New Paradigm for MRI Reconstruction

Introduction

MRI reconstruction has moved beyond the simple Fast Fourier Transform, towards more complicated parallel imaging and non-linear reconstruction algorithms. Often, developers who wish to implement and deploy their advanced algorithms on clinical scanners, find the vendor supported reconstruction hardware is inadequate for advanced algorithms or the provided programming environment is not suitable for clinical integration. The open-source framework, the Gadgetron, which was published recently, aims to address some of these concerns [1]. With this framework, algorithms can be implemented on suitable hardware selected by the user and subsequently connected to the scanner. While this is a valuable step-forward, the original Gadgetron was designed to run the reconstruction task within one process residing on a single computer and does not provide explicit support for cloud computing across multiple computational nodes. Although multiple CPU or GPU cores on one computer can contribute to the computation, single computer may not carry sufficient computing power to achieve clinical usage of non-linear reconstruction. To remove this limitation, we have extended the Gadgetron framework to support cloud computing. With this extension (named "Gadgetron Plus or GT-Plus"), any number of Gadgetron processes can run across multiple computers (thereafter referred as 'nodes') and a dedicated inter-process controlling scheme is implemented to multiple nodes. We demonstrate with the GT-Plus cloud non-linear reconstruction of real-time cardiac cine imaging can be deployed in a clinical setting with acceptable reconstruction latency. Specifically, a multi slice real-time cine acquisition covering cardiac ventricles and non-linear reconstruction can be completed within 1 min.

Architecture and Implementation

Figure 9:
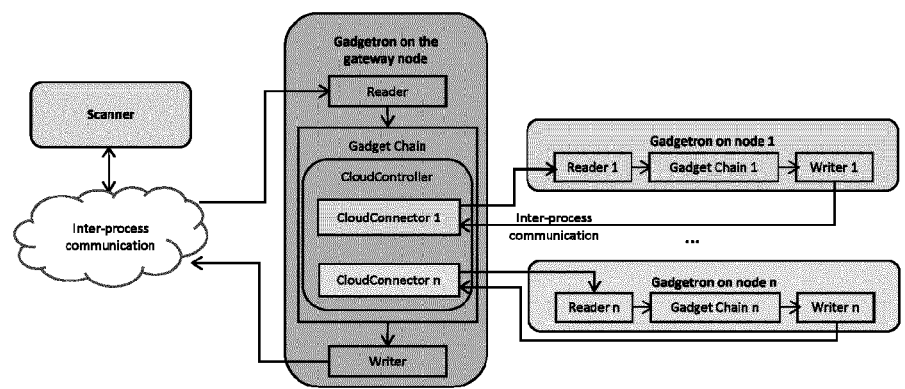
FIG. 9 depicts a schematic outline of typical setup of GT-Plus cloud. Here at least one Gadgetron process is running on a node (Multiple Gadgetron processes can run in one node on different ports). The gateway node communicates with the client application (e.g. MRI scanner). It manages the connections to each computing node via the software module GadgetCloudController and GadgetronCloudConnector. Whenever sufficient data is buffered on the gateway node, the packages can be sent to the computing node for processing. Different computing nodes can run completely different reconstruction chains. The Reader/Writer module in each Gadgetron process serializes/deserializes data to/from the Gadget chain for processing.

Schematic outline of GT-Plus is shown in FIG. 9, representing a typical set up of Gadgetron based cloud where at least one Gadgetron running on a specific port at each node. A software module GadgetCloudController is implemented to manage the communication between nodes via TCP/IP sockets. Typically, a gateway node receives readout data from the scanner and distributes them through the cloud. For every connected node, a reader thread (CloudReaderTask) and a writer thread (CloudWriterTask) is spawned as active objects. There is a Gadgetron processing chain running on every connect node and for different cloud nodes. different processing chains can be performed. Whenever the reconstruction results are sent back from a cloud node, the gateway is notified and will take actions defined by the user, e.g. forwarding images back to the scanner or waiting for other jobs to complete.

Deployment

The GT-Plus package can be deployed on various platforms. Two cloud setups were tested here. Amazon EC2 based cloud 19 nodes were launched to build up a virtual cloud on the Amazon Elastic Compute Cloud (Amazon EC2). Every node has two eight-core Intel Xeon E5-2670 2.60 GHz processors and 60 GB RAM, running Ubuntu Server 13.10. NIH Biowulf cluster The Biowulf system (http://biowulf.nih.gov) is a GNU/Linux parallel processing system built at the National Institutes of Health, USA. A total of 38 nodes were requested from the Biowulf. The gateway node had two eight-core Intel Xeon E5-2670 2.60 GHz processors and 72 GB RAM. All other nodes have two six-core Intel Xeon X5660 2.80 GHz processors and 24 GB RAM. For both setups, the "online" reconstruction was achieved.

In-Vivo Test

Cloud based reconstruction was performed for multi-slice free-breathing myocardial cine imaging with non-linear l1-SPIRiT reconstruction [3]. A healthy volunteer (female, 23.8 yrs) was scanned on a 1.5T clinical MRI system (MAGNETOM Area, Siemens, 32-channel surface coil). Acquisition parameters were: balanced SSFP readout, TR=2.35/TE=1.04 ms, acquired matrix 192×100, flip angle 60°, FOV 320×240 $mm^2$, slice thickness 8 mm with a gap of 2 mm, bandwidth 723 Hz/pixel, interleaved acquisition pattern with acceleration factor R=5. The ventricles of the heart were covered by 9 slices and for every slice the acquisition lasted 1.5 s with one dummy heartbeat between slices.

Results

Figure 10:
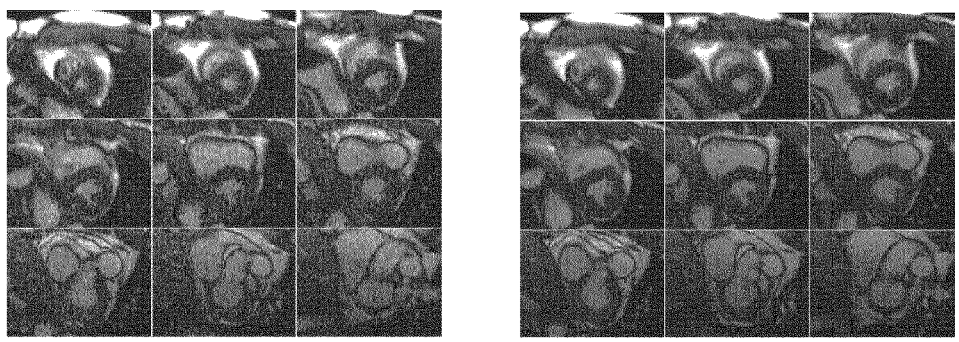
FIG. 10 depicts reconstruction results of multi-slice myocardial cine imaging on the GT-Plus cloud. Compared to the Grappa linear reconstruction shown on the left, non-linear reconstruction on the right gives noticeable improvement in image quality. For this 9-slice cine protocol with entire ventricular coverage, the cloud version of non-linear reconstruction was completed within 30 s after the end of data acquisition, while the single-node reconstruction took ~9 mins. This significant reduction of computing time could be crucial for clinical usage of advanced image reconstruction techniques.
Figure 11:
Figure 12:
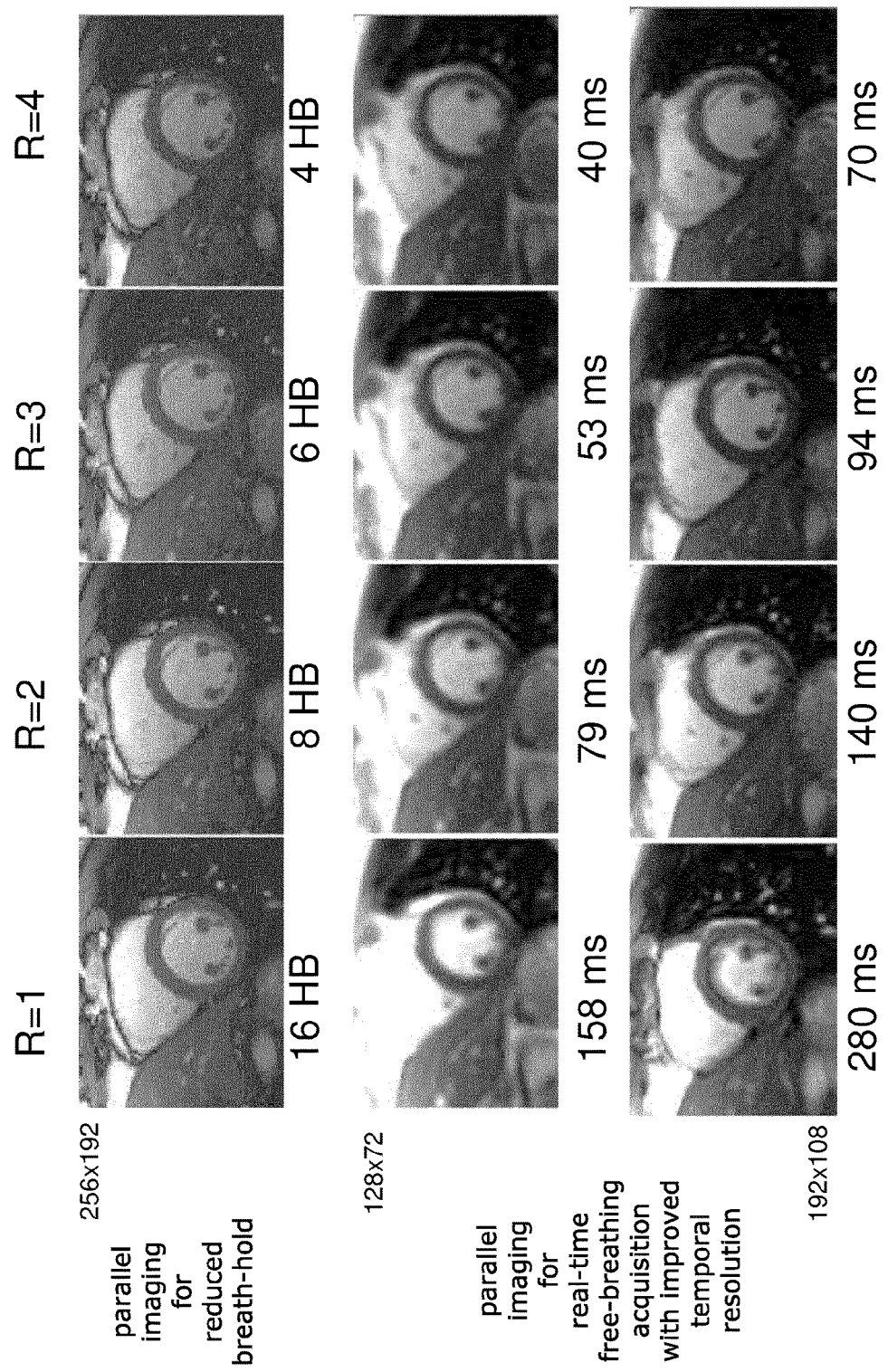
Figure 14:
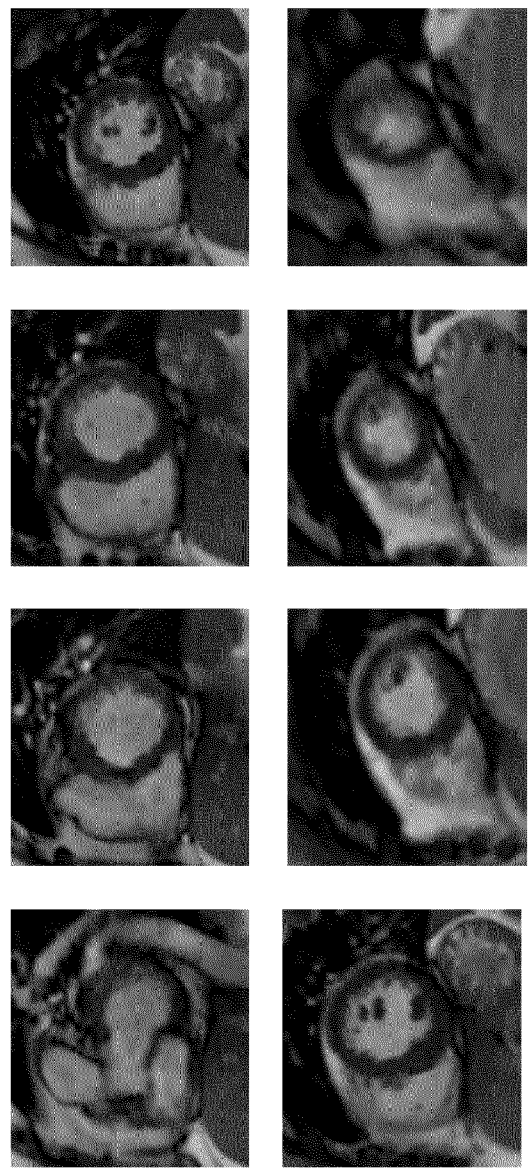
Figure 15:
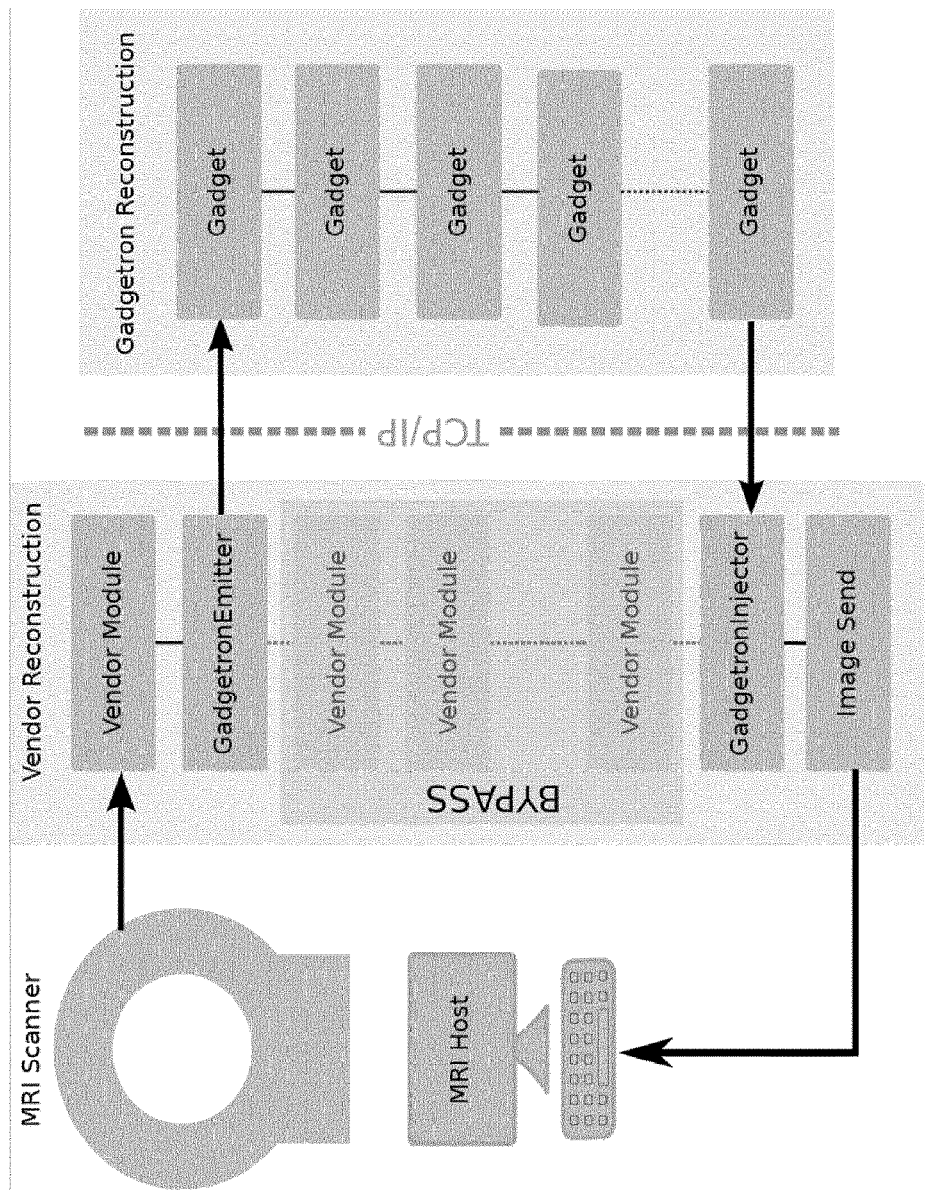
Figure 16:
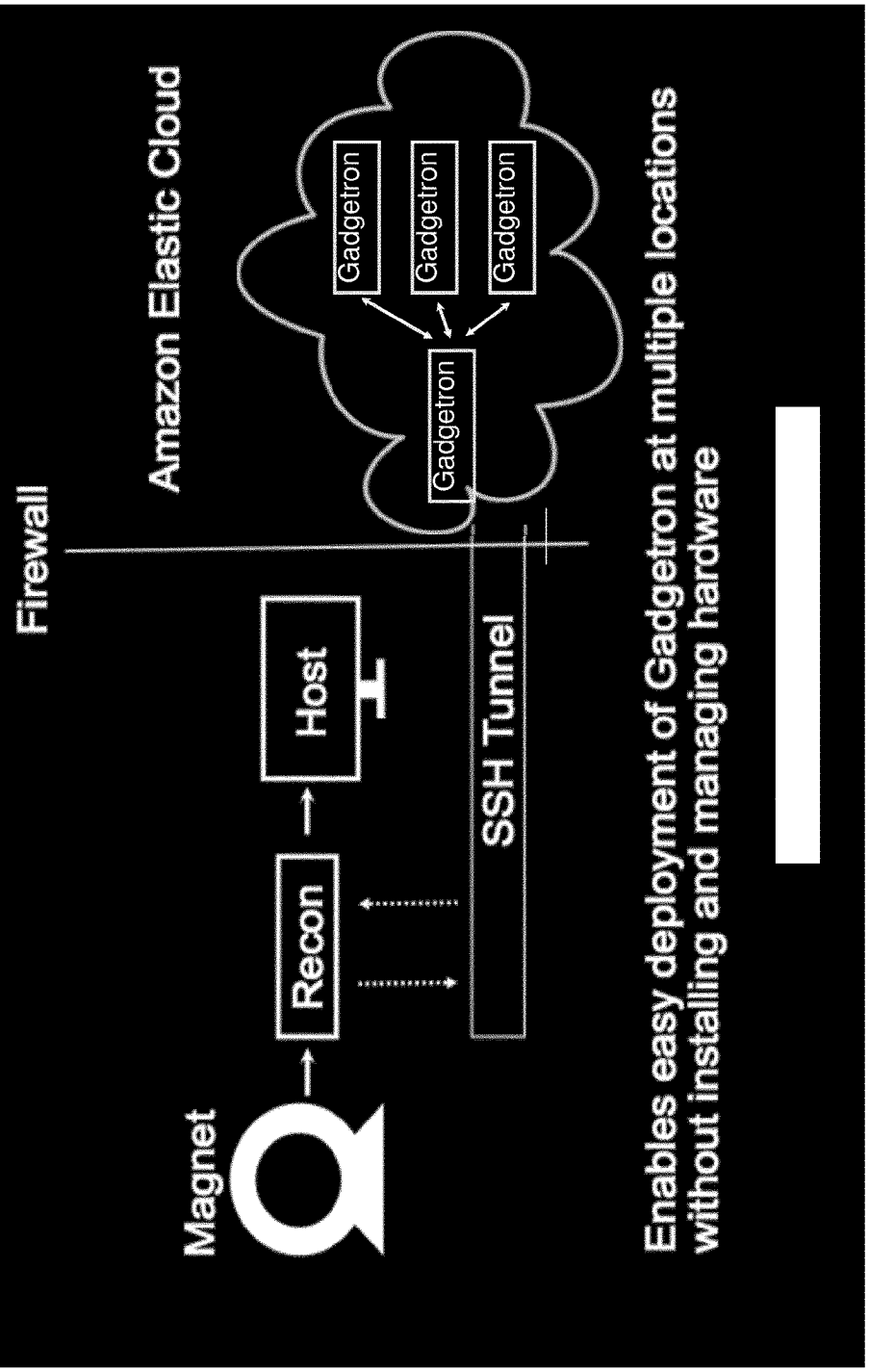
Figure 17:
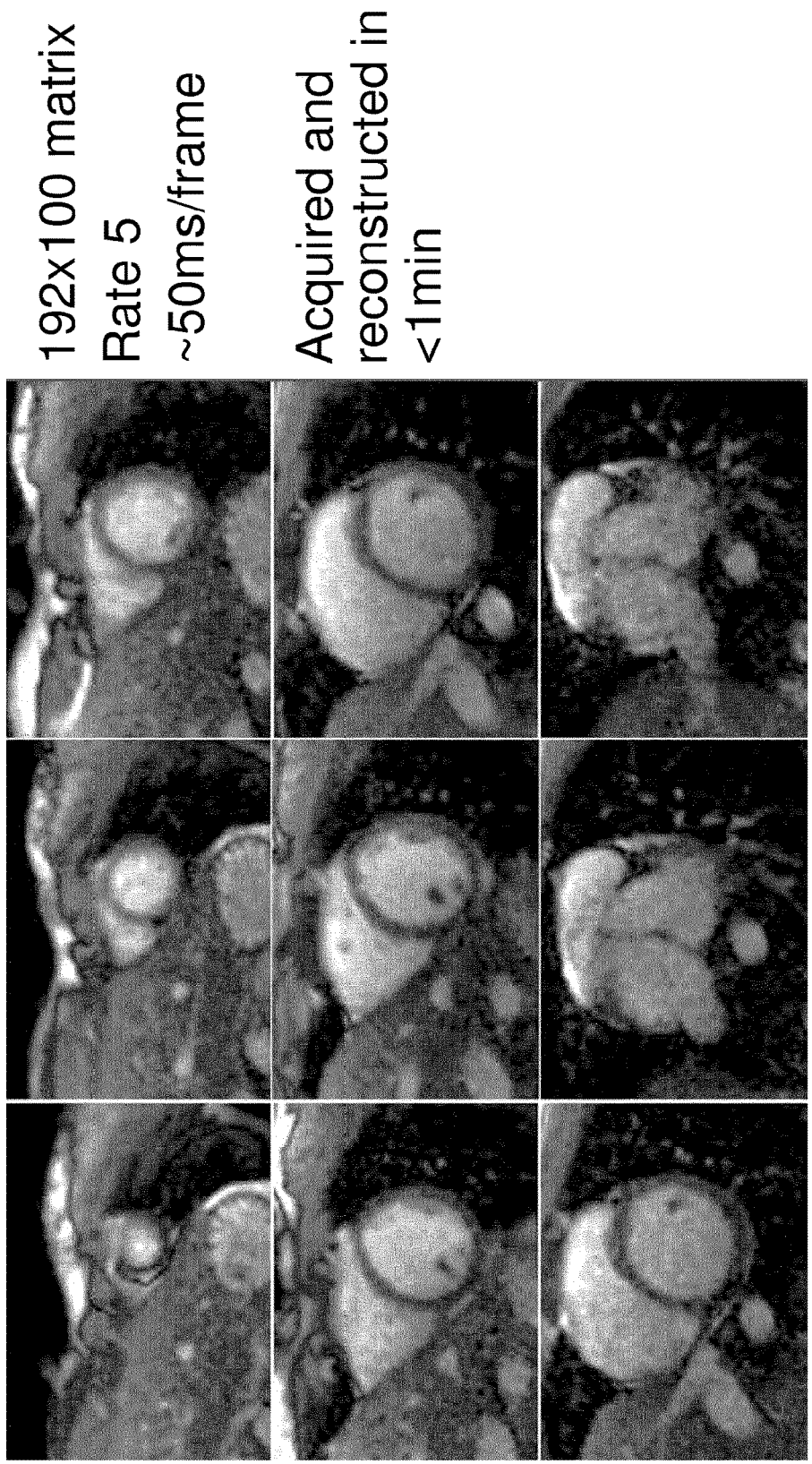
Figure 19:
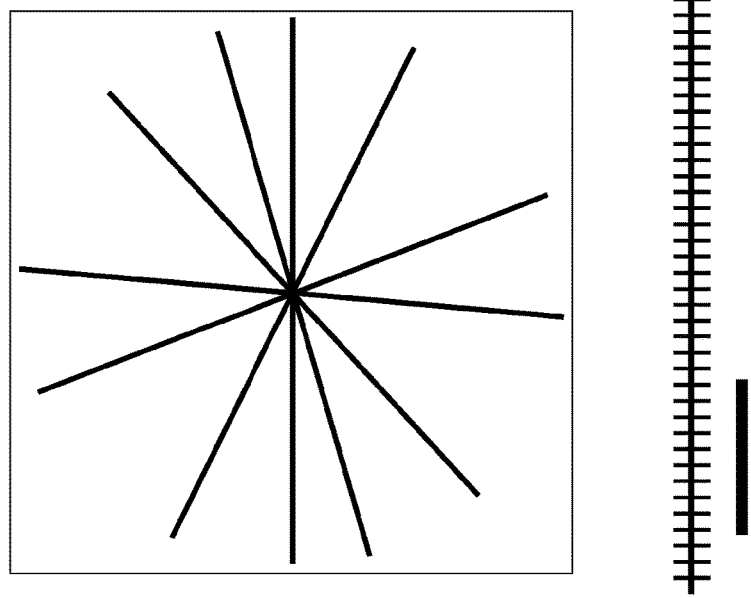
Figure 20:
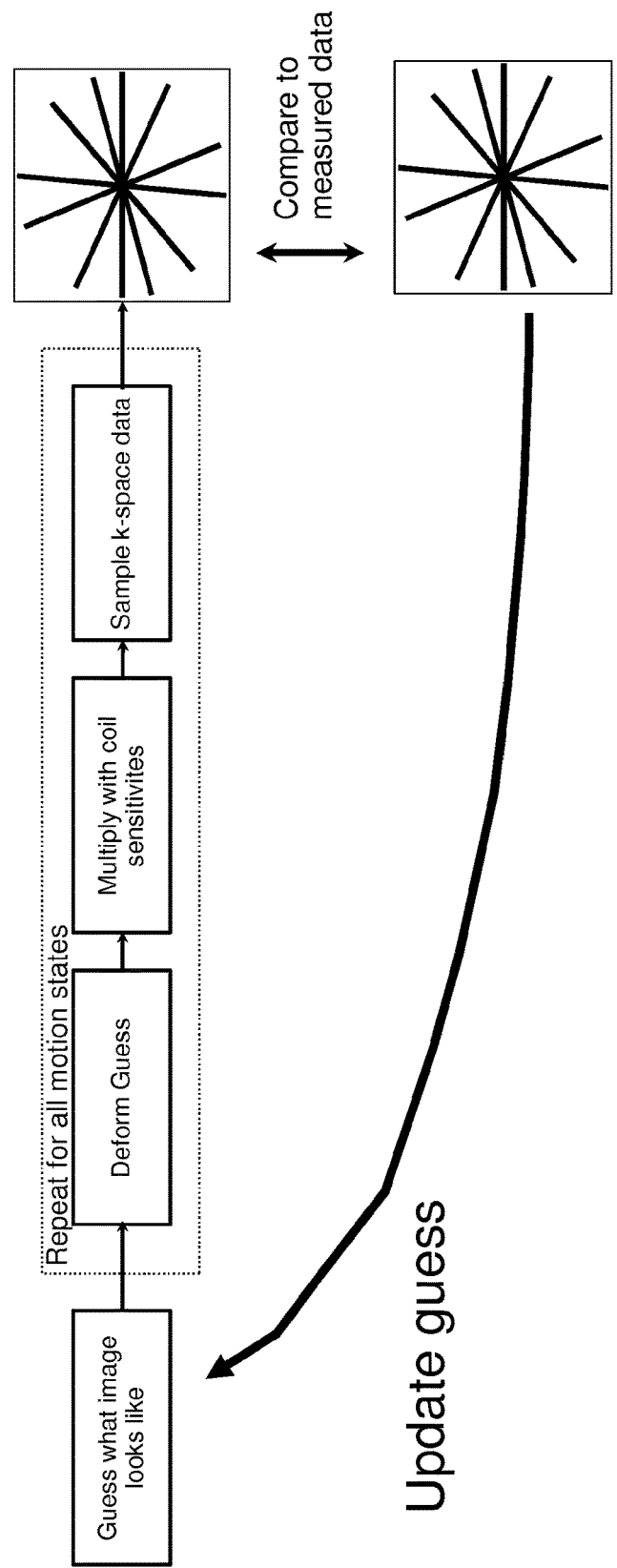
Figure 21:
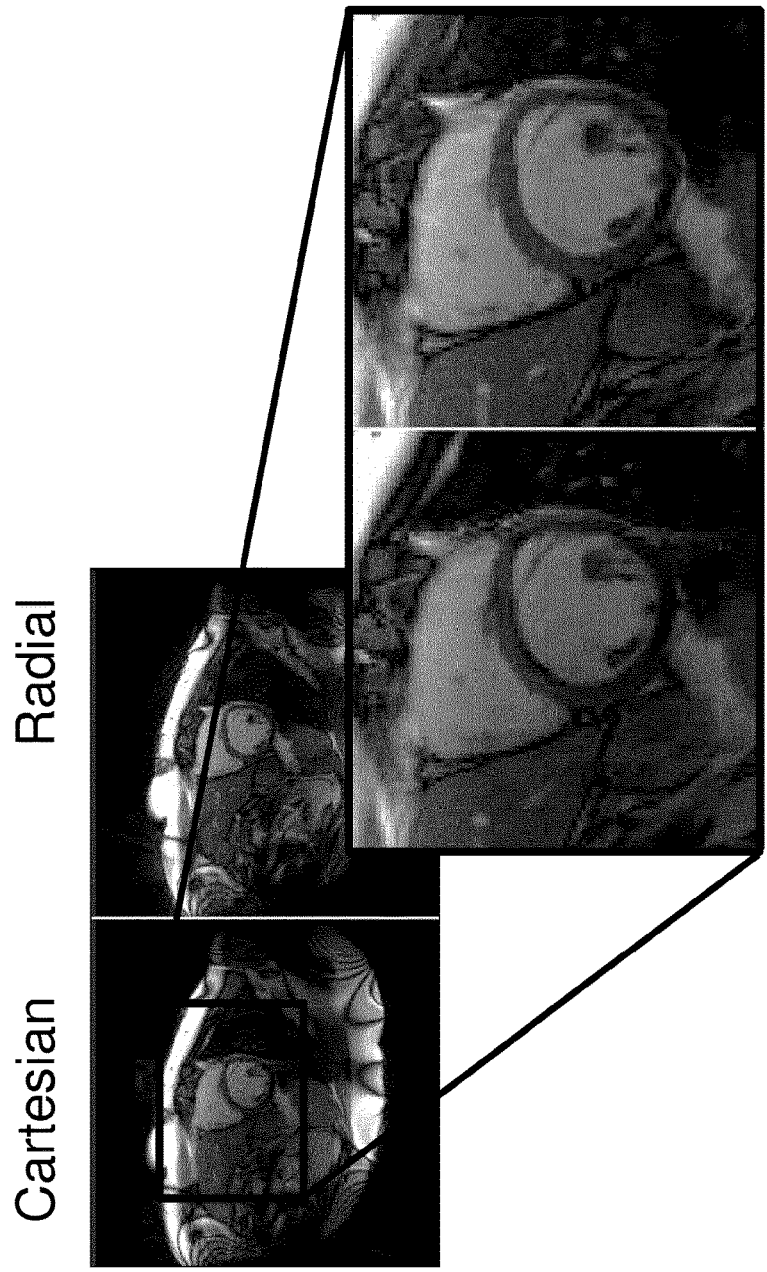
Figure 22:
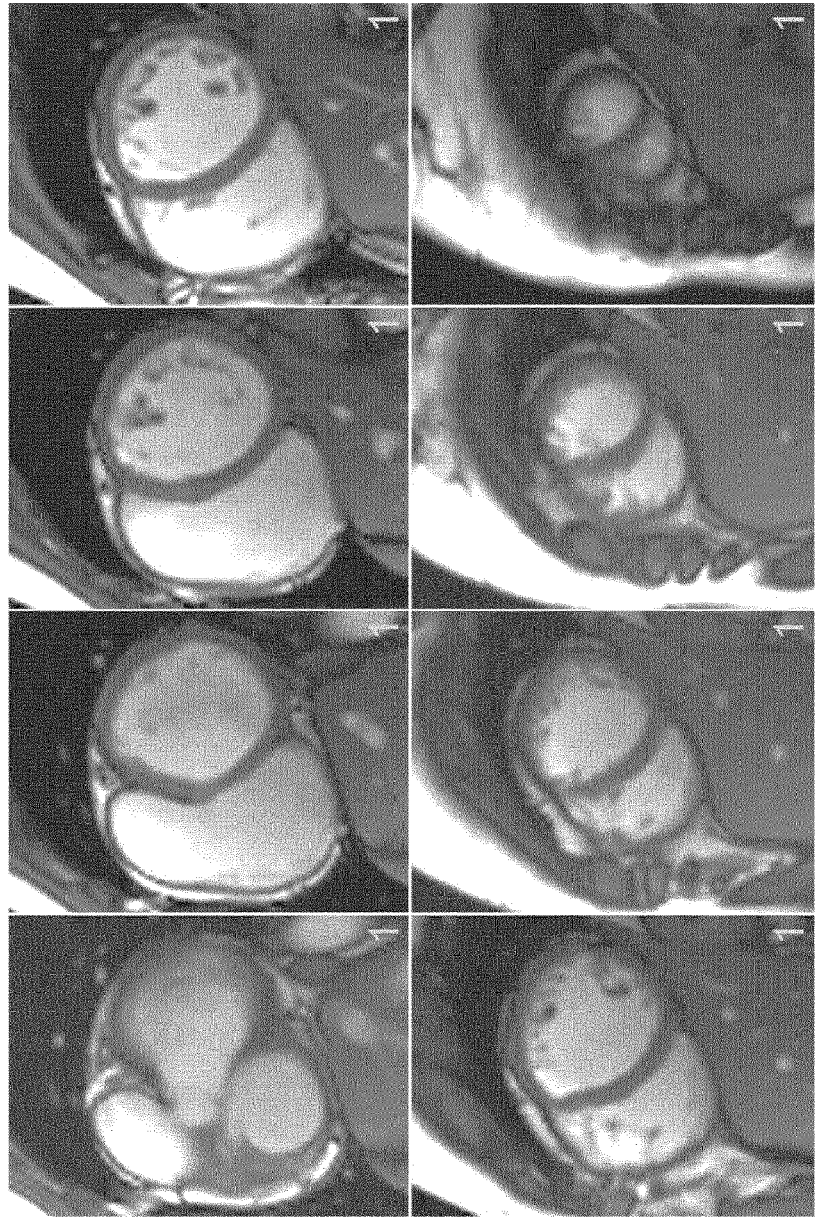
Figure 23:
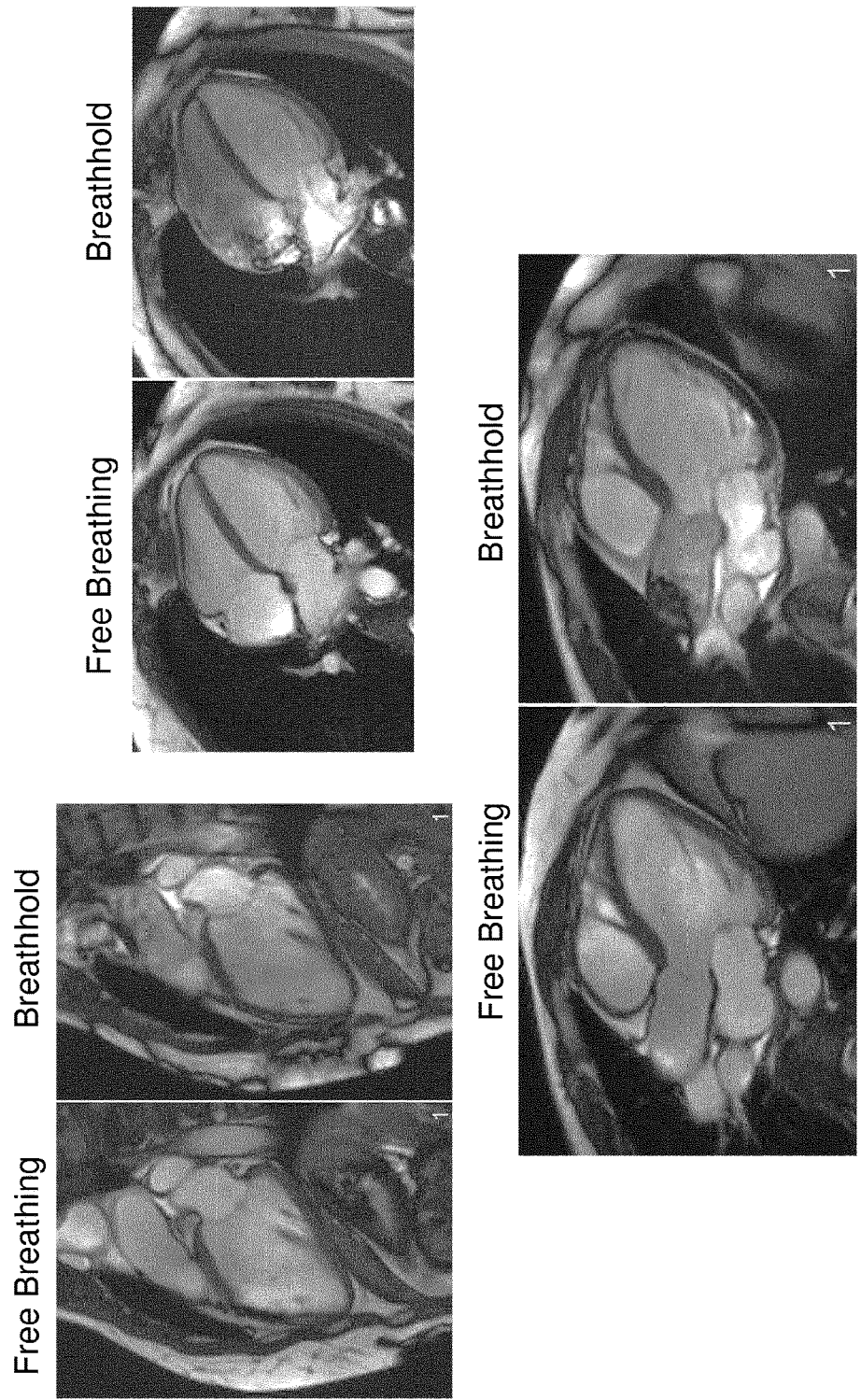
Figure 24:
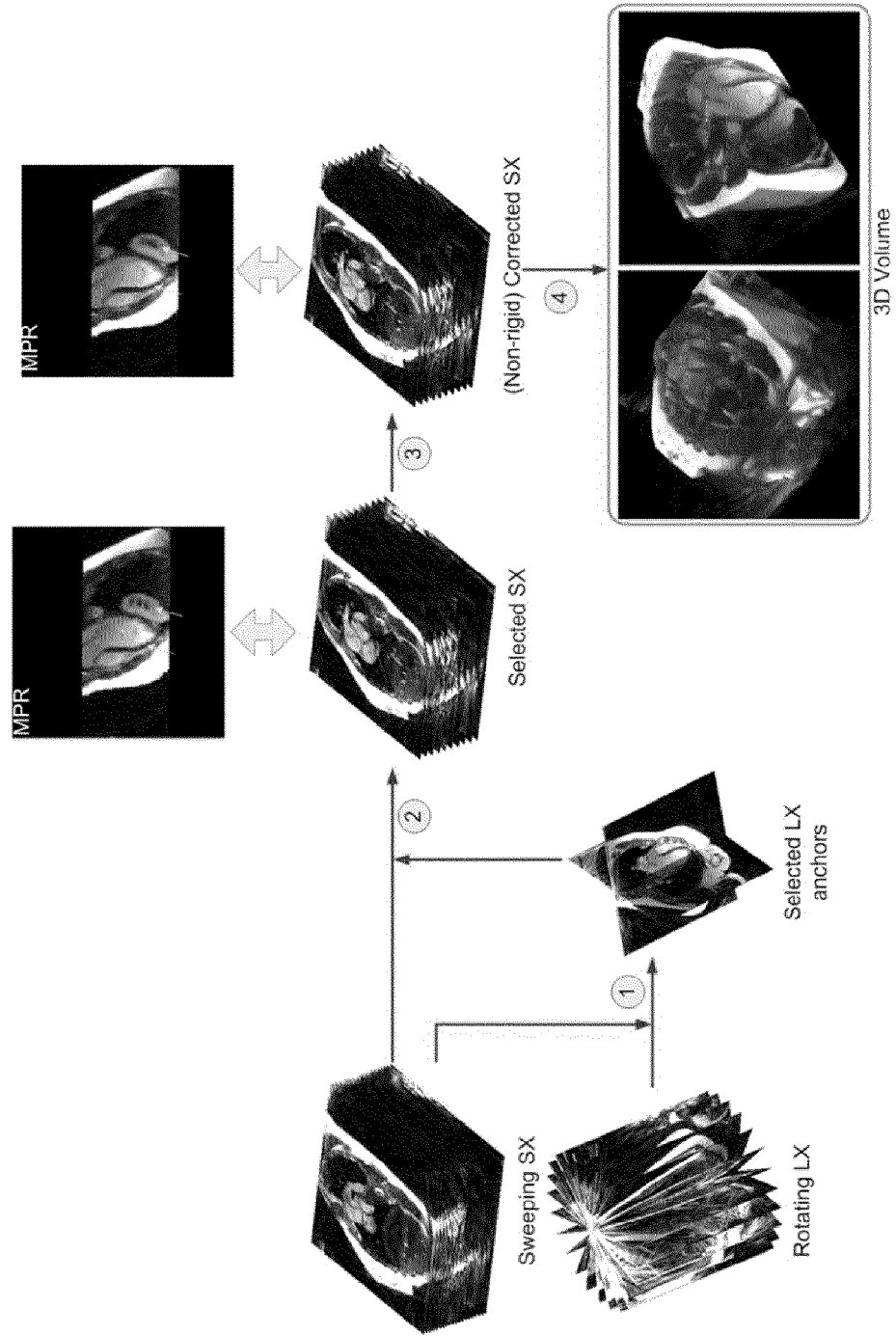

FIG. 10 shows the reconstruction results generated on the GT-Plus based cloud, illustrating noticeable improvement in image quality using non-linear reconstruction. The scan time (defined as the time to perform data acquisition) for this test was 22.6 s. On the described Amazon EC2 cloud, the total imaging time (defined as the time from the start of data acquisition to the moment when images of all slices were sent back to the scanner) was 52.6 s. The computing time (defined as the time used to perform the reconstruction computation) was 48.9 s. Note the reconstruction started once the first slice was acquired, rather than waiting for the completion of all 9 slices. On the NIH's Biowulf cloud, imaging and computing times were 62.1 s and 58.2 s. If only the single gateway node was used, the computing time was 427.9 s and 558.1 s for two cloud setups respectively.

Conclusions

The GT-Plus extension for the Gadgetron framework was developed to support cloud computing over multiple computing nodes. As a demo, the increased computational power significantly speeds up the l1-SPIRiT reconstruction for multi-slice cine imaging, enabling the 1 min imaging for whole left ventricular coverage with significant improvement in image quality. On the other hand, the framework is independent from specific use cases and can be applied to other MRI applications.

REFERENCES

[1] Hansen M S, et al., MRM 69:1768-1776 (2013)
[2] Lustig M, et al., MRM 64:457-471

What is claimed is:

1. A system for generating reconstructed images comprising:
    a client computing device for generating raw image data for a subject, the raw image data comprising one or more image parameters;
    at least one database comprising:
        a list of modeling rules for selecting a target computational model based on image parameters included in the raw image data; and
        a network address location for each of a plurality of reconstruction systems, each reconstruction system executing at least one different target computational model to generate a reconstructed image data from the raw image data; and a computation power index associated with each of the reconstruction systems, the computation power index indicating computational capabilities of each reconstruction system;
at least one processor; and
an application comprising modules executable by the at least one processor to:
process received raw image data from the client computing device to identify a target computational model based on the list of modeling rules;
determine a computational load based on image parameters included in the received raw image data;
identify a corresponding network address location for one of the plurality of the reconstruction system executing the target computational model, based on the associated computation power index and the computational load required for reconstructing the raw image data;
transmit the received image data to the corresponding network address location for the reconstruction system associated with a computation power index capable of accommodating the required computation load, to generate reconstructed image data; and
retrieve the reconstructed image data for display.

2. The system of claim 1 wherein the client computing device is a magnetic resonance image (MRI) scanner.

3. The system of claim 1 wherein the client computing device is a computed tomography (CT) scanner.

4. The system of claim 1 wherein the client computing device is an ultrasound scanner.

5. The system of claim 1 wherein the identified network address location corresponds to Uniform Resource Locator (URL) address on the Internet.

6. The system of claim 1 wherein the reconstruction system comprises:
a reader to de-serialize the raw image data received from the client computing device;
at least a second processor to execute the target computational model in response to the raw image data and generate the reconstructed image data; and
a writer to serialize the reconstructed image data for transmission to the at least one processor.

7. The system of claim 1 wherein the one or more image parameters specify a two-dimensional image type or a three-dimensional image type.

8. The system of claim 7 wherein the application executable by the at least one processor is further configured to:
transmit the received raw image data to a first corresponding network address location for a first reconstruction system to generate the reconstructed image data when the image parameters specify a two-dimensional image type; and
transmit the received raw image data to a second corresponding network address location for a first reconstruction system to generate the reconstructed image data when the image parameters specify a three-dimensional image type.

9. The system of claim 1 wherein the application executable by the at least one processor is further configured to transmit the received raw image data to the corresponding network address location over a communication network selected from one of a group consisting of a wide area network and a local area network.

10. The system of claim 1 wherein the one or more image parameters are selected from the group consisting of a spatial dimension parameter, a time parameter, a flow/velocity parameter, an experiment timing dimension parameter, a diffusion encoding parameter, a functional/physiological testing dimension parameter, and physiologic gating index parameter.

11. An apparatus for processing system raw image data for image reconstruction comprising:
at least one processor; and
a memory comprising:
a list of modeling rules identifying a target computational model based on image parameters included in raw image data; and
a network address location for each of a plurality of reconstruction systems, each reconstruction system executing a different target computational model to generate reconstructed image data from the raw image data;
a computation power index associated with each of the reconstruction systems, the computation power index indicating computation capabilities of each reconstruction system; and
an application comprising modules executable by the at least one processor to control routing of the raw image data to a reconstruction system for processing, the application comprising:
an input module to receive raw image data from an image scanner;
a computation identification module to identify a target computational model based on the list of modeling rules, and to identify a computational load based on image parameters included in the received raw image data;
an address module to identify a corresponding network address location for the reconstruction system executing the target computational model, based on the associated computation power index and the computational load required for reconstructing the raw image data; and
a communication module to:
transmit the received raw image data to the corresponding network address location for the reconstruction system associated with a computation power index capable of accommodating the required computational load, to generate reconstructed image data; and
retrieve the reconstructed image data for display.

12. The apparatus of claim 11 wherein the input module receives the raw image data from a magnetic resonance image (MRI) scanner.

13. The apparatus of claim 11 wherein the input module receives the raw image data from a computed tomography (CT) scanner.

14. The apparatus of claim 11 wherein the input module receives the raw image data from an ultrasound scanner.

15. The apparatus of claim 11 wherein the identified network address location correspond to Uniform Resource Locator (URL) address on the Internet.

16. The apparatus of claim 11 wherein the reconstruction system comprises:
a reader to de-serialize the raw image data received from the image scanner;
at least a second processor to:
execute the target computational model in response to the raw image data; and
generate the reconstructed image data; and
a writer to serialize the reconstructed image data and transmit transmission to the at least one processor.

17. The apparatus of claim 11 wherein the one or more image parameters specify a two-dimensional image type or a three-dimensional image type.

18. The apparatus of claim 17 wherein:
the communication module is further configured to:
transmit the received raw image data to a first corresponding network address location for a first reconstruction system to generate the reconstructed image data when the image parameters specify a two-dimensional image type; and
transmit the received raw image data to a second corresponding network address location for a first reconstruction system to generate the reconstructed image data when the image parameters specify a three-dimensional image type.

19. The apparatus of claim 11 wherein the communication module is further configured to transmit the received raw image data to the corresponding network address location over a communication network selected from one of a group consisting of a wide area network and a local area network.

20. The apparatus of claim 11 wherein the one or more image parameters are selected from the group consisting of a spatial dimension parameter, a time parameter, a flow/velocity parameter, an experiment timing dimension parameter, a diffusion encoding parameter, a functional/physiological testing dimension parameter, and a physiologic gating index parameter.

* * * * *